US008828932B2

(12) United States Patent
Jiang et al.

(10) Patent No.: US 8,828,932 B2
(45) Date of Patent: Sep. 9, 2014

(54) BIFUNCTIONAL MOLECULES FOR INACTIVATING HIV AND BLOCKING HIV ENTRY

(75) Inventors: Shibo Jiang, Fresh Meadows, NY (US); Chungen Pan, Guangzhou (CN); Lu Lu, Luoyang (CN)

(73) Assignee: New York Blood Center, Inc., New York, NY (US)

( * ) Notice: Subject to any disclaimer, the term of this patent is extended or adjusted under 35 U.S.C. 154(b) by 316 days.

(21) Appl. No.: 13/100,031

(22) Filed: May 3, 2011

(65) Prior Publication Data

US 2011/0269676 A1    Nov. 3, 2011

Related U.S. Application Data

(60) Provisional application No. 61/330,787, filed on May 3, 2010.

(51) Int. Cl.
| | | |
|---|---|---|
| A61K 38/16 | (2006.01) | |
| A61K 39/42 | (2006.01) | |
| A61P 31/18 | (2006.01) | |
| C07K 14/00 | (2006.01) | |
| C07K 14/16 | (2006.01) | |
| C07K 14/005 | (2006.01) | |
| C07K 14/73 | (2006.01) | |

(52) U.S. Cl.
CPC ........... *C07K 14/005* (2013.01); *C07K 2319/32* (2013.01); *A61K 38/162* (2013.01); *C07K 14/70514* (2013.01); *C12N 2740/16122* (2013.01)
USPC ............ 514/3.8; 514/21.2; 514/3.9; 530/350; 424/148.1

(58) Field of Classification Search
None
See application file for complete search history.

(56) References Cited

U.S. PATENT DOCUMENTS

| | | | |
|---|---|---|---|
| 5,444,044 | A | 8/1995 | Jiang et al. |
| 7,144,991 | B2 * | 12/2006 | Goshorn et al. ........... 530/391.7 |
| 7,456,251 | B2 | 11/2008 | Dwyer et al. |
| 2002/0094521 | A1 | 7/2002 | Wild et al. |
| 2004/0122214 | A1 | 6/2004 | Bray et al. |

FOREIGN PATENT DOCUMENTS

| | | |
|---|---|---|
| WO | 03/016333 A2 | 2/2003 |
| WO | 2004/104033 A2 | 12/2004 |
| WO | 2005/007831 A2 | 1/2005 |
| WO | 2006/105199 A2 | 10/2006 |
| WO | 2008/019817 A1 | 2/2008 |
| WO | 2009/155064 A1 | 12/2009 |

OTHER PUBLICATIONS

Fontenot, et al., Structure-based design of peptides that recognize the CD4 binding domain of HIV-1 gp120. AIDS, 12(12):1413-8, 1998.*
Vermeire, et al., Anti-HIV agents targeting the interaction of gp120 with the cellular CD4 receptor, Expert Opin. Investig. Drugs, 14(10):1199-1212, 2005.*
Münch, et al., Discovery and Optimization of a Natural HIV-1 Entry Inhibitor Targeting the gp41 Fusion Peptide, Cell 129, 263-275, Apr. 20, 2007.*
Chan et al. "HIV Entry and Its Inhibition." Cell, vol. 93, 681-684, May 29, 1998.
Fouts et al. "Expression and characterization of a single-chain polypeptide analogue of the human immunodeficiency virus type 1 gp120-CD4 receptor complex." Journal of Virology, vol. 74, No. 24, Dec. 1, 2000, pp. 11427-11436.
Haim et al. "Soluble CD4 and CD4-Mimetic Compounds Inhibit HIV-1 Infection by Induction of a Short-Lived Activated State." PLOS Pathogens, Apr. 2009, vol. 5, Issue 4.
Huang et al. "Identification of the HIV-1 gp41 core-binding motif—HXXNPF." FEBS Letters 580 (2006) 4807-4814.
International Search Report for PCT/US2011/035007.
Jiang et al. "Enhancement of Human Immunodeficiency Virus Type 1 Infection by Antisera to Peptides from the Envelope Glycoproteins gp120/gp41." J. Exp. Med., vol. 174, Dec. 1991, 1557-1563.
Jiang et al. "HIV-1 inhibition by a peptide." Nature, vol. 365, Sep. 9, 1993.
Joshi et al. "A core trimmer of the paramyxovirus fusion protein: parallels to influenza virus hemaglutinin and HIV-1 GP41." Virology, vol. 248, No. 1, Oct. 1, 1998, pp. 20-34.
Liu et al. "Different from the HIV Fusion Inhibitor C34, the Anti-HIV Drug Fuzeon (T-20) Inhibits HIV-1 Entry by Taregting Multiple Sites in gp41 and gp120." The Journal of Biological Chemistry, vol. 280, No. 12, Issue of Mar. 25, pp. 11259-11273, 2005.
Liu et al. "HIV gp41 C-terminal Heptad Repeat Contains Multifunctional Domains." Journal of Biological Chemistry, vol. 282, No. 13, Mar. 30, 2007, pp. 9612-9620.
Lu et al. "Surface Exposure of the HIV-1 Env Cytoplasmic Tail LLP2 Domain during the Membrane Fusion Process." Journal of Biological Chemistry, vol. 283, No. 24, pp. 16723-16731, Jun. 13, 2008.
Papanikolopoulou et al. "Formation of Highly Stable Chimeric Trimers by Fusion of an Adenovirus Fiber Shaft Fragmane with the Foldon Domain of Bacteriophage T4 Fibritin." Journal of Biological Chemistry, Vo. 279, No. 10, Issue of Mar. 5, pp. 8991-8998, 2004.
Tan et al. "Atomic structure of a thermostable subdomain of HIV-1 gp41." Proceedings of the National Academy of Sciences, vol. 94, No. 23, Nov. 11, 1997, pp. 12303-12308.
Wild et al. "Peptides corresponding to a predictive alpha-helical domain of human immunodeficiency virus type 1 gp41 are potent inhibitors or virus infection." Proceedings of the National Academy of Sciences, vol. 91, Oct. 1, 1994, pp. 9770-9774.
He, Y et al. "Identification of a critical motif for the human immunodeficiency virus type 1 (HIV-1) gp41 core structure: implications for designing novel anti-HIV fusion inhibitors." J. Virol. 82:6349-6358, 2008.
Liu, S. et al. "HIV gp41 C-terminal heptad repeat contains multifunctional domains." J. Biol. Chem. 282:9612-20, 2007.

* cited by examiner

*Primary Examiner* — Satyanarayana R Gudibande
(74) *Attorney, Agent, or Firm* — K&L Gates LLP; Louis C. Cullman; Michelle Glasky Bergman

(57) ABSTRACT

Disclosed herein are bifunctional molecules which inactivate human immunodeficiency virus (HIV) even before the virus attacks the target cell and inhibits HIV entry into the target cell. Also disclosed are novel anti-HIV therapeutics for treatment of patients infected by HIV. Further disclosed are methods for prophylaxis against HIV and treatment of HIV infection.

3 Claims, 14 Drawing Sheets

FIG. 6A FIG. 6B FIG. 6C
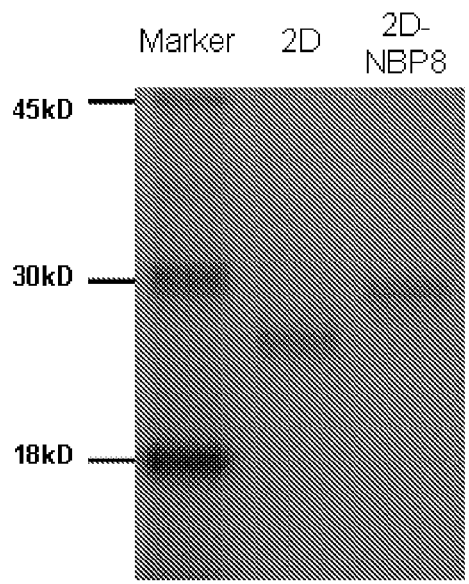
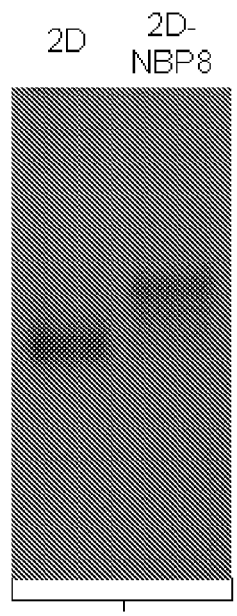
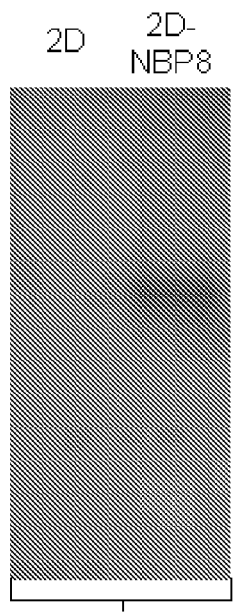
Western blot by anti-CD4 antibody
Western blot by anti-T1144 antibody
FIG. 7
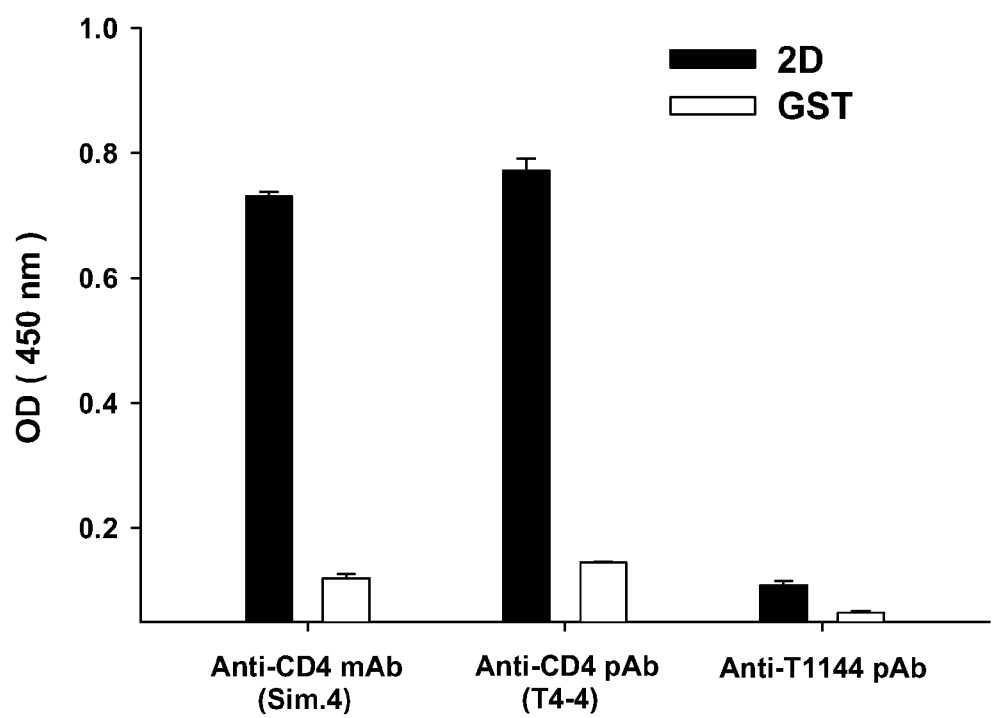

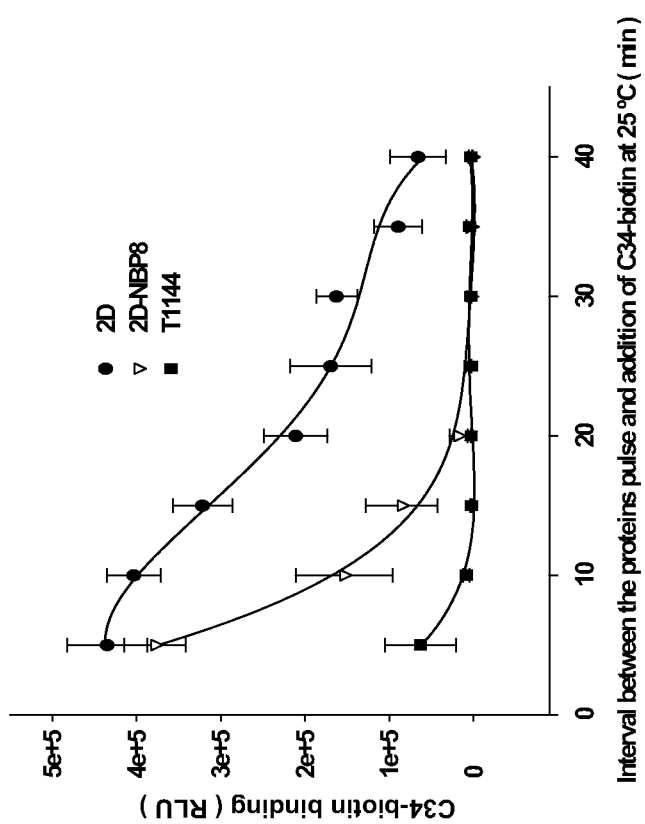
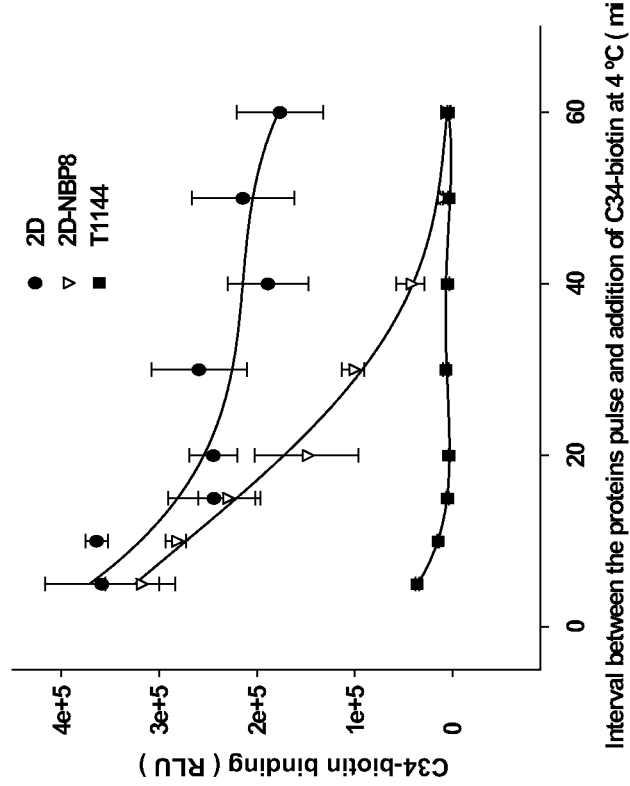
FIG. 19

BIFUNCTIONAL MOLECULES FOR INACTIVATING HIV AND BLOCKING HIV ENTRY

CROSS-REFERENCE TO RELATED APPLICATIONS

This application claims the benefit under 35 U.S.C. §119(e) to provisional patent application 61/330,787 filed May 3, 2011, the entire contents of which is incorporated by reference herein.

FIELD OF THE INVENTION

The field of this disclosure related to peptide compounds for treating human immunodeficiency virus-related diseases.

BACKGROUND OF THE INVENTION

By the end of 2007, about 33.2 million people in the world are living with human immunodeficiency virus (HIV) infection and more than 25 million people have died of Acquired Immunodeficiency Syndrome (AIDS). Therefore, it is urgently needed to discover and develop new therapeutic strategies against HIV infection. So far, 28 anti-HIV drugs have been approved by the Food and Drug Administration of the United States to treat people infected with HIV, including 15 reverse transcriptase inhibitors (RTIs), 10 protease inhibitors (PIs), one integrase inhibitor (II), and two entry inhibitors (EIs). All the RTIs, PIs, and II inhibit HIV replication after the virus enters the host cells. The two EIs can block HIV entry into the host cell, but they cannot inactivate virus before HIV attaches to the target cell.

One of the EIs is a synthetic peptide designed based on the sequence of the HIV envelope protein (Env) transmembrane subunit gp41 C-terminal heptad repeat (CHR) region, named T20 (enfuvirtide, FUZEON®), which inhibits HIV fusion with the host cell by targeting gp41. T20 inhibits HIV entry by targeting HIV envelope protein (Env) gp41, which consists of fusion peptide (FP), and N- and C-terminal heptad repeats (NHR and CHR) (FIG. 1). In the native state, gp41 is inaccessible since it is buried underneath HIV Env gp120. At the beginning of HIV infection process, gp120 binds to CD4 on the target cell, causing gp41 to change conformation: (1) FP inserts into the target cell membrane; (2) NHR associates to form an NHR-trimer, and (3) CHR interacts with NHR-trimer to form a hairpin-like six-helix bundle (6-HB) which brings the viral and cellular membranes into close proximity which is necessary for fusion. T20 and C34, another CHR peptide (CP) can bind to the viral gp41 NHR-trimer and block 6-HB formation, resulting in inhibition of HIV fusion. However, T20 cannot inactivate HIV circulating in the blood before the virus attaches to the target cell because it can only interact with HIV after the virus comes into contact with CD4 on the target cell. Because of this problem, the T20 peptide must be maintained in the blood of HIV/AIDS patients at a constant high concentration. Therefore, T20 has to be administrated by injection twice a day at 90 mg/dose, resulting in painful injection-site reactions in most patients and high cost to the patients (>$20,000/year/patient). Consequently, T20 is exorbitantly expensive for use in developing countries. Therefore, improved drugs for treating HIV infection and AIDS are needed.

BRIEF DESCRIPTION OF THE DRAWINGS

FIG. 6 depicts SDS-PAGE (FIG. 6A) and Western blot (FIGS. 6B and 6C) analysis of the purified 2D and 2D-NBP8.

FIG. 7 depicts the biological character of the 2D (D1D2 domain of sCD4). Polyclonal antibodies (T4-4), conformation-dependent Sim.4 monoclonal antibody against CD4, and polyclonal antibodies against NBP8 were used to detect bound recombinant 2D molecule.

FIGS. 11A and 11E depict the sCD4 control and FIGS. 11D and 11H depict the NBP8 control.

FIG. 12A—Binding of 2D with gp120. FIG. 12B—Binding of 2D-NBP8 with gp120. FIG. 12C—Binding of NBP8 with gp120.

FIGS. 14A and 14C—FN-PAGE analysis. FIGS. 14B and 14D—Coomassie blue staining of FN-PAGE gel.

FIG. 19 depicts the destabilization by 2D-NBP8 of 2D-activated envelope glycoprotein intermediate through interacting with exposed N-HR domain at 4° C. (FIG. 19A) and 25° C. (FIG. 19B).

SUMMARY OF THE INVENTION

Figure 1:
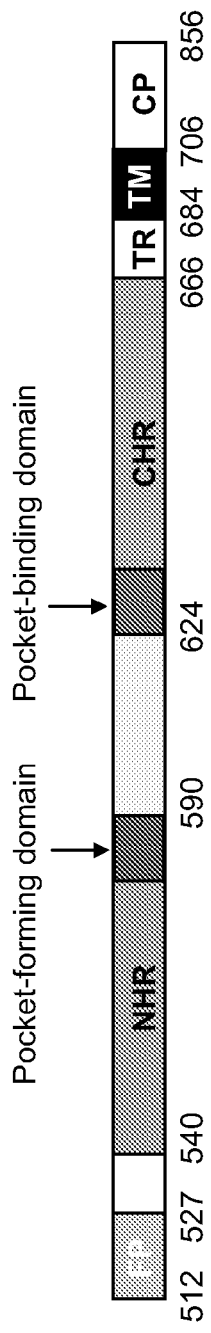
FIG. 1 depicts a schematic view of gp41 functional domains. The residue number corresponds to its position in HIV-1$_{HXB2}$ gp160. FP, fusion peptide; TR, tryptophan-rich region; TM, transmembrane domain; CP, cytoplasmic domain.
Figure 2:
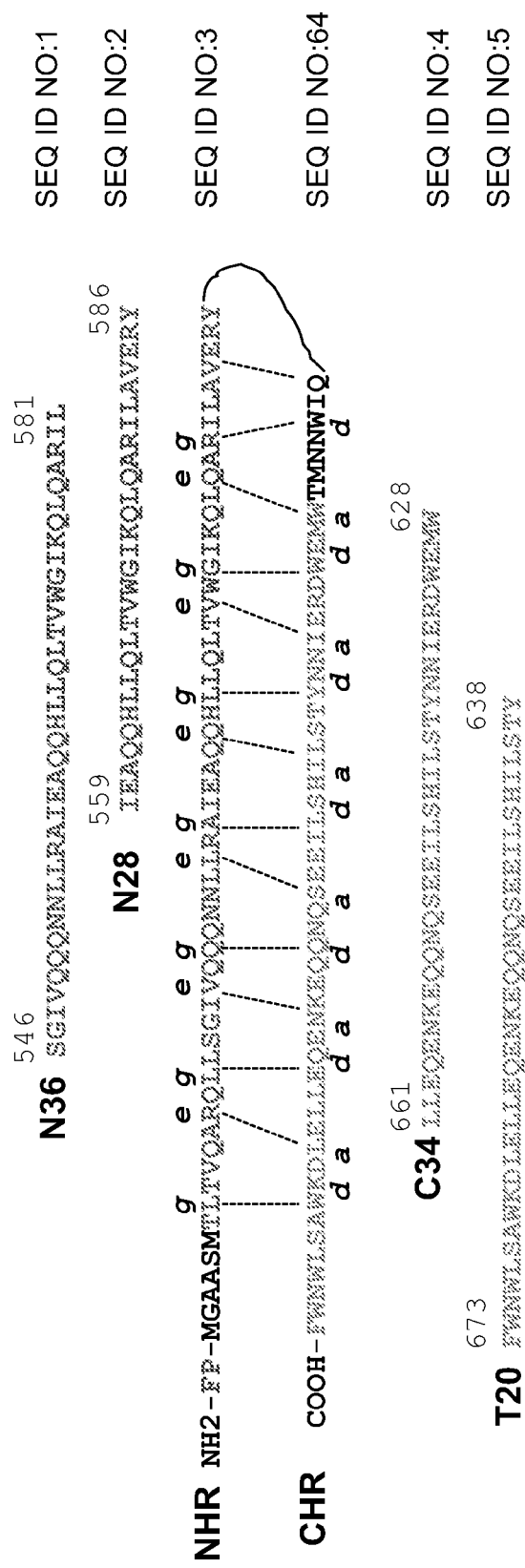
FIG. 2 depicts interactions between the N-terminal heptad repeat (NHR) and C-terminal heptad repeat (CHR) of gp41 and between N- and C-peptides. The dashed lines between NHR and CHR indicate the interaction between the residues located at the e and g positions in the NHR and the a and d positions in the CHR.
Figure 3:
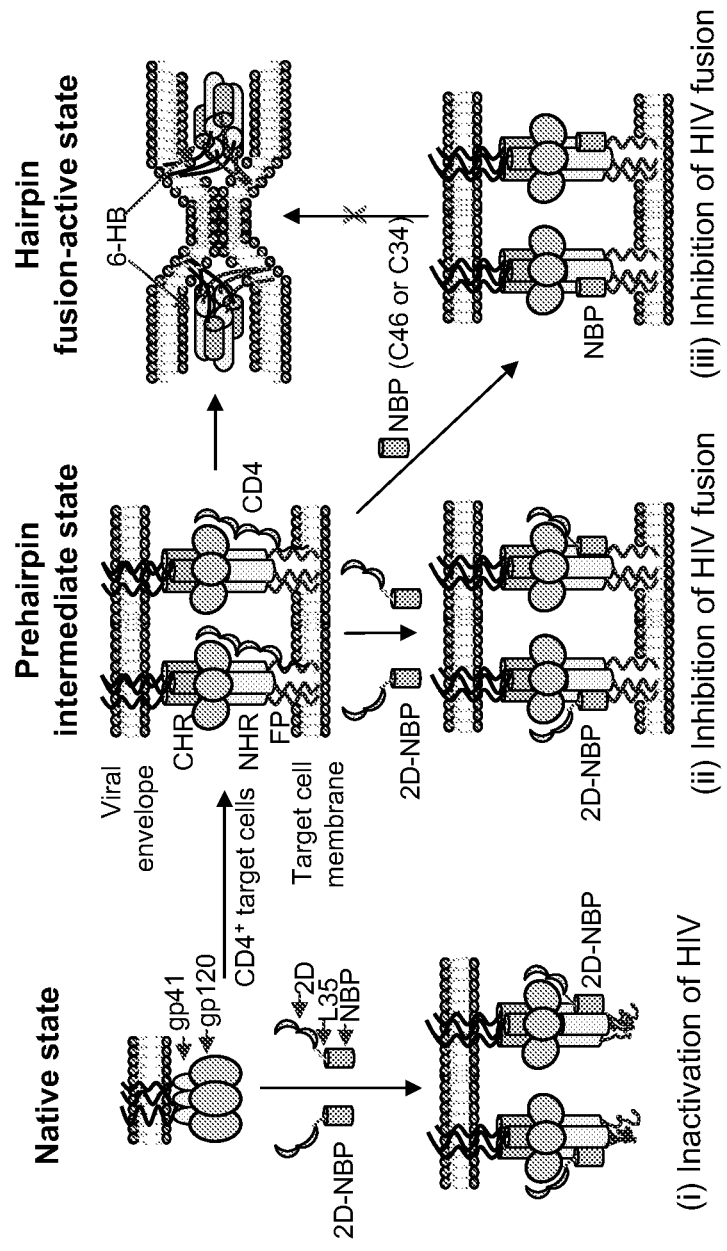
FIG. 3 depicts a model of gp41-mediated HIV fusion and mechanisms of action of NHR-binding protein (NBP) and a bifunctional molecule, 2D-NBP. The NBP (e.g., C46, C34, T1144, and T20) binds to gp41 NHR, resulting in inhibition of HIV with the target cell (iii). 2D-NBP binds to gp120, via its 2D domain, and interacts, via NBP domain, with gp41 NHR, leading to irreversible inactivation of HIV (i). Like NBP, 2D-NBP can also inhibit virus fusion with the target cell (ii).
Figure 4:
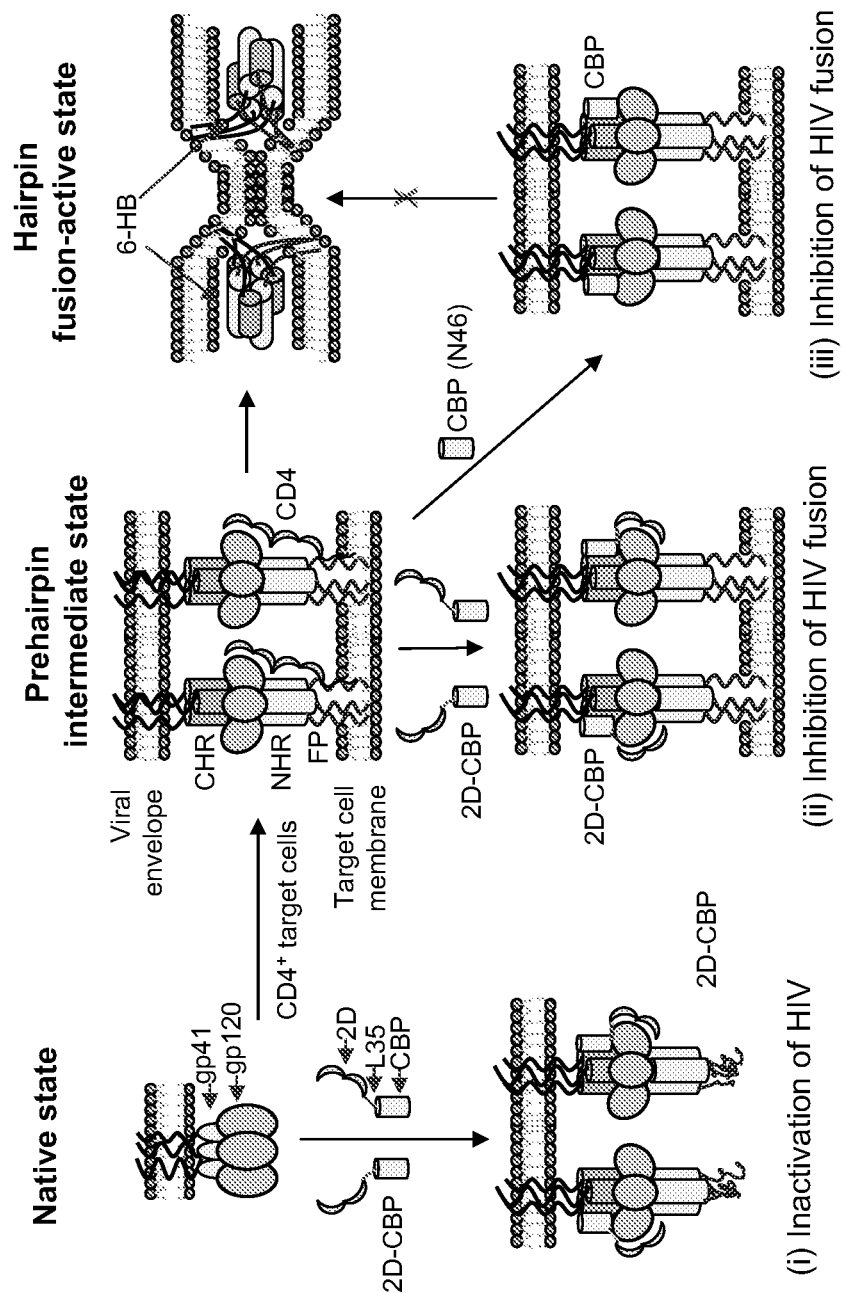
FIG. 4 depicts a model of gp41-mediated HIV fusion and mechanisms of action of CHR-binding protein (CBP) and a bifunctional molecule, 2D-CBP. The CBP (e.g., N46 and N36) binds to gp41 CHR, resulting in inhibition of HIV with the target cell (iii). 2D-CBP binds to gp120, via its 2D domain and interacts, via CBP domain, with gp41 CHR, leading to irreversible inactivation of HIV (i). Like CBP, 2D-CBP can also inhibit virus fusion with the target cell (ii).
Figure 5:
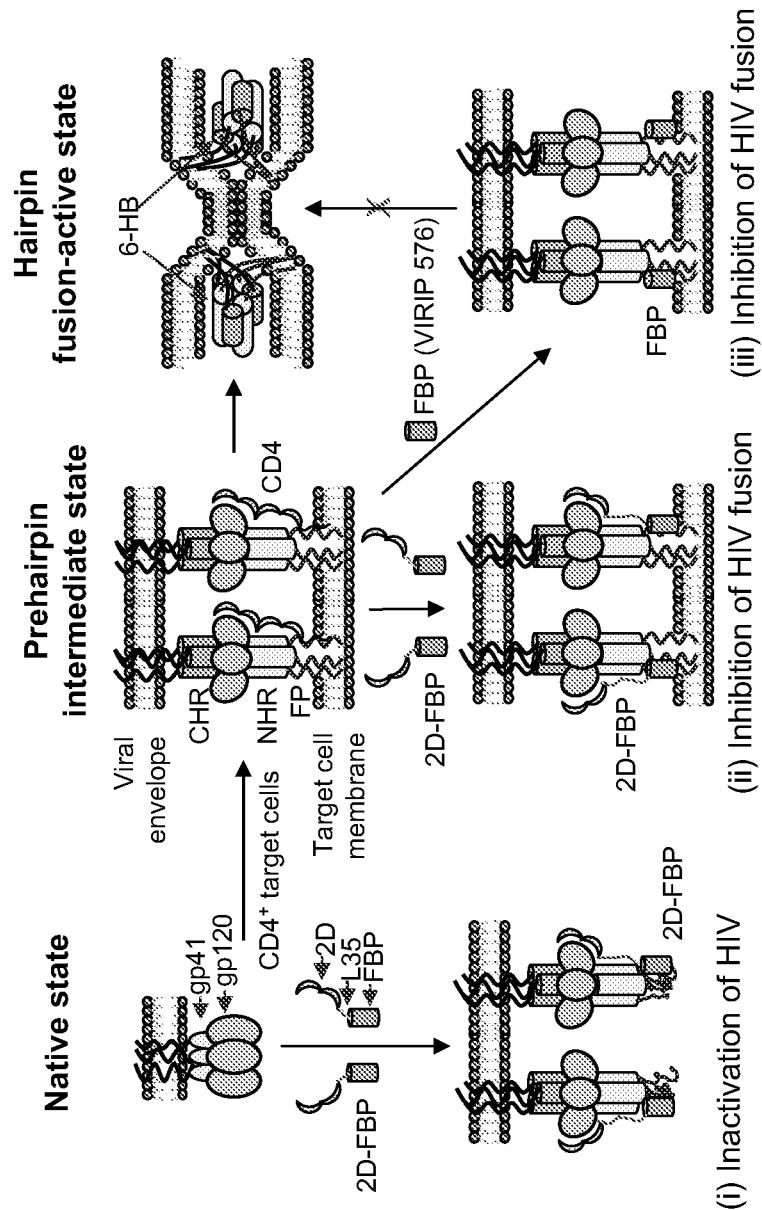
FIG. 5 depicts the model of gp41-mediated HIV fusion and mechanisms of action of FP-binding protein (FBP) and a bifunctional molecule, 2D-FBP. The FBP (e.g., VIRIP-1) binds to gp41 FP, resulting in inhibition of HIV with the target cell (iii). 2D-FBP binds to gp120, via its 2D domain, and interacts via FBP domain, with gp41 NHR, leading to irreversible inactivation of HIV (i). Like FBP, 2D-FBP can also inhibit virus fusion with the target cell (ii).

Bifunctional molecules (designated 2D-CP) are disclosed herein which contain: (i) a soluble CD4 (sCD4) or D1D2 domain of sCD4 (2D), which can bind to gp120 to trigger a conformational change in gp41, leading to exposure of the NHR, CHR and FP; (ii) a NHR-, CHR- or FP-binding peptide (CP) which can interact with the gp41 NHR, CHR or FP, respectively; (iii) a flexible linker consisting of 10 to 40 amino acids ((GGGGS)$_n$, wherein n=2-8) to link the 2D and CP so that these two functional domains can move freely to bind corresponding target proteins on HIV or HIV-infected cells.

These bifunctional molecules inactivate HIV even before the virus attacks the target cell and inhibit HIV entry into the target cell. These molecules can be further developed as novel anti-HIV therapeutics for treatment of patents infected by HIV, including non-B and multi-drug resistant strains, through a mechanism of action that is different from current anti-HIV drugs.

In one embodiment disclosed herein, a pharmaceutical composition is provided comprising a polypeptide comprising a first domain comprising a soluble CD4 or a portion of soluble CD4; a second domain comprising a human immunodeficiency virus (HIV) gp41 functional domain-binding sequence selected from the group consisting of N-terminal heptad repeat (NHR)-binding peptides, C-terminal heptad repeat (CHR)-binding peptides and fusion peptide (FP)-binding peptides; and a flexible linker linking the amino acid sequences of the first domain and the second domain, wherein the linker comprises the amino acid sequence (GGGGS)$_n$, wherein n is an integer between 2 and 8.

In another embodiment, the portion of soluble CD4 comprises the D1D2 domain of sCD4. In another embodiment, the NHR-binding peptide is selected from the group consisting of C46, C38, C36, C34, C28, C51, sifuvirtide, T1144, CP621-652, CP32M, T1249, PBD-4HR, CBD1, and T20; the CHR-binding peptide is selected from the group consisting of N46, N36, N34, N51, DP107, N17, and N28; and the FP-binding peptide is selected from the group consisting of VIRIP164, VIRIP165, VIRIP353, and VIRIP576.

In yet another embodiment, the polypeptide comprises an amino acid sequence selected from the group consisting of SEQ ID NOs:37-62.

In yet another embodiment, the composition further includes at least one pharmaceutically acceptable excipient.

In one embodiment, disclosed herein, a method of treating a viral infection is provided comprising administering an effective dose of the disclosed pharmaceutical composition to an individual exposed to an HIV infection; inactivating HIV, and blocking entry of HIV into a target cell, thereby treating the viral infection. In another embodiment, the pharmaceutical composition comprises a polypeptide comprising an amino acid sequence selected from the group consisting of SEQ ID NOs:37-62.

In one embodiment disclosed herein, a method of preventing a viral infection is provided comprising administering an effective dose of the disclosed pharmaceutical composition to an individual who has been exposed to or will be exposed to HIV; inactivating HIV, and blocking entry of HIV into a target cell, thereby preventing the viral infection. In another embodiment, the pharmaceutical composition is administered topically to prevent sexual transmission of HIV. In yet another embodiment, the pharmaceutical composition comprises a polypeptide comprising an amino acid sequence selected from the group consisting of SEQ ID NOs:37-62.

DETAILED DESCRIPTION OF THE INVENTION

Bifunctional molecules (designated 2D-CP) are disclosed herein which contain: (i) a first domain comprising a soluble CD4 (sCD4) or D1D2 domain of sCD4 (2D), which can bind to gp120 to trigger a conformational change in gp41, leading to exposure of the gp41 N-terminal heptad repeat (NHR), C-terminal heptad repeat (CHR) or fusion peptide (FP); (ii) a second domain comprising a NHR-, CHR- or FP-binding peptide (CP) which can interact with the gp41 a NHR-, CHR- or FP, respectively; (iii) and a flexible linker consisting of 10 to 40 amino acids ((GGGGS)$_n$, wherein n=2-8) to link the first domain (2D) and second domain (CP) so that these two functional domains can move freely to bind corresponding target proteins on human immunodeficiency virus (HIV) or HIV-infected cells. The designed molecules are expressed in *E. coli* or 293T cells, purified by chromatography and tested for their inhibitory activity on HIV-mediated cell-cell fusion and HIV replication, as well as for their ability to inactivate cell-free and cell-associated HIV.

Disclosed herein are a series of bifunctional molecules, designated D1D2-NHR-binding peptide (2D-NBP), D1D2-CHR-binding peptide (2D-CBP), and D1D2-FP-binding peptide (2D-FBP), which inactivate HIV by binding to gp120 and gp41 NHR, CHR or FP, via 2D (D1D2 domain of soluble CD4) and NBP, CBP, or FBP, respectively, and/or to inhibit HIV fusion and entry into the target cell by interacting with the gp41 pre-hairpin intermediate structure through its NHR, CHR or FP domain. These hybrid molecules can function as a double guard in that 1) they kill HIV before the virus comes into contact with the target cells; and 2) they block HIV entry into the target cell after the virus attaches to the cell, in case the virus has escaped the first attack by the molecules.

The disclosed bifunctional molecules have great potential to be developed as novel anti-HIV therapeutics that can be used in both developing and developed countries. Compared with the current anti-HIV drugs, 2D-CPs have unique mechanism of action, namely inactivation of HIV. Because their mechanism of action is different from those of other anti-HIV drugs in clinical use, 2D-CPs are expected to be effective against HIV isolates with multiple drug resistance. The combination of 2D-CPs with other anti-HIV drugs may have synergistic anti-HIV effects. Compared with the T20 peptide, 2D-CPs have higher in vivo efficacy, since they can both inactivate HIV that circulates in the blood at any given time and can also inhibit HIV fusion and entry. In comparison, T20 can only inhibit HIV fusion during a brief time window (<20 minutes), i.e. during gp41's conformational change from the native to intermediate state, which is triggered by gp120 binding to the CD4⁺ target cell. Therefore, lower dosages and less frequent injections of 2D-CPs than T20 may be required to eliminate HIV in blood or reduce the viral load. Consequently, 2D-CPs will be less costly to patients and cause them less suffering from injection-site reactions. Furthermore, 2D-CPs, as recombinant proteins, may have lower production cost (since they can be expressed on a large scale) and a higher stability and half-life (because of its larger molecular size) than the synthetic peptide T20, and therefore are expected to be more affordable for developing countries.

Exemplary CPs include, but are not limited to, C46 (SEQ ID NO:6), C38 (SEQ ID NO:7), C36 (SEQ ID NO:8), C34 (SEQ ID NO:4), C28 (SEQ ID NO:9), C51 (SEQ ID NO:10), sifuvirtide (SEQ ID NO:11), T1144 (SEQ ID NO:12), C35-EK (SEQ ID NO:63), CP621-652 (SEQ ID NO:13), CP32M (SEQ ID NO:14), T1249 (SEQ ID NO:15), PBD-4HR (SEQ ID NO:16), CBD1 (SEQ ID NO:17), T20 (SEQ ID NO:5), N46 (SEQ ID NO:18), N36 (SEQ ID NO:1), N34 (SEQ ID NO:19), N51 (SEQ ID NO:20), DP107 (SEQ ID NO:21), N17 (SEQ ID NO:22), N28 (SEQ ID NO:2), VIRIP164 (SEQ ID NO:23), VIRIP165 (SEQ ID NO:24), VIRIP353 (SEQ ID NO:25), and VIRIP576 (SEQ ID NO:26).

Moreover, pharmaceutical compositions are disclosed herein which are 85%, 90%, 91%, 92%, 93%, 94%, 95%, 96%, 97%, 98%, 99% or 100% identical to the amino acid sequences of SEQ ID NOs: 37-62. Identity or homology with respect to such sequences is defined herein as the percentage of amino acid residues in the candidate sequence that are identical with SEQ ID NOs: 37-62, after aligning the sequences and introducing gaps, if necessary, to achieve the maximum percent homology, and not considering any conservative substitutions as part of the sequence identity. Fusion proteins, or N-terminal, C-terminal or internal extensions, deletions, or insertions into the peptide sequence shall not be construed as affecting homology.

Thus, the proteins disclosed herein include molecules having the amino acid sequence of SEQ ID NOs:37-62; amino acid sequence variants wherein one or more amino acid residues has been inserted N- or C-terminal to, or within, the disclosed coding sequence; and amino acid sequence variants of the disclosed sequence, or their fragments as defined above, that have been substituted by at least one residue. Such fragments, also referred to as peptides or polypeptides, may contain antigenic regions, functional regions of the protein identified as regions of the amino acid sequence which correspond to known protein domains, as well as regions of pronounced hydrophilicity. The regions are all easily identifiable by using commonly available protein sequence analysis software such as MACVECTOR™ (Oxford Molecular).

As used herein, the designation of an amino acid residue in the instant peptides as more than one amino acid (using the common one-letter amino acid code) in parenthesis with a slash between the amino acids, means that any of the indicated amino acids, or mimetics thereof (unless specifically excluded), could occupy that residue. For example, (I/L/V)(T/S/A/V/C) means that the first residue can be any one of isoleucine, leucine, or valine, and the second residue can be any one of threonine, serine, alanine, valine, or cysteine, or mimetics.

The amino acid residues for the disclosed peptides include conservative amino acid substitutions. For example, conservative amino acid changes may be made which, although they alter the primary sequence of the protein or peptide, do not normally alter its function. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine.

The present disclosure is also directed to pharmaceutical compositions comprising the above-described bifunctional peptides that can inhibit HIV entry into a target cell, in a pharmaceutically acceptable carrier.

Dosages and desired drug concentrations of the disclosed pharmaceutical compositions may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. The term "therapeutically effective" amount as used herein refers to the amount needed to perform the particular treatment for a disease such as, for example, an infectious disease. "Treatment" refers to both therapeutic treatment and prophylactic or preventative measures, wherein the object is to prevent or slow down (lessen) the targeted pathologic condition or disease. Those in need of treatment include those already with the disease as well as those prone to have the disease or those in whom the disease is to be prevented. In one embodiment, the disease is present. In another embodiment, the life of a cell or an individual is prolonged due to the methods described herein.

2D-CPs have the potential to be developed as novel anti-HIV therapeutics for treating patients infected by HIV, including non-B and multi-drug resistant strains, as prophylactic agents for pre- and post-exposure prophylaxis of HIV infection, and as microbicides for prevention of sexual transmission of HIV.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal and intrabuccal administration can be made without undue experimentation by means well known in the art, for example with an inert diluent or with an pharmaceutically acceptable carrier. The compositions are enclosed in gelatin capsules or compressed into tablets. For the purpose of oral therapeutic administration, the pharmaceutical compositions may be incorporated with excipients and used in the form of tablets, troches, capsules, elixirs, suspensions, syrups, wafers, chewing gums and the like. A "pharmaceutically acceptable carrier" means any of the standard pharmaceutical carriers. Examples of suitable carriers are well known in the art and may include but are not limited to any of the standard pharmaceutical carriers like phosphate buffered saline solutions, phosphate buffered saline containing Polysorb 80, water, emulsions such as oil/water emulsion, and various types of wetting agents. Other carriers may also include sterile solutions, tablets, coated tablets, and capsules. Typically such carriers contain excipients like starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Tablets, pills, capsules, troches and the like may also contain binders, excipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories, enemas, gels, creams, tablets, and the like. Suppository formulations can easily be made by methods known in the art. Similarly, vaginal administration forms comprising suppositories, gels, douches, creams, tablet, rings and the like can be formulated. The composition may be intended for rectal or vaginal administration, in the form, e.g., of a suppository which will melt in the rectum and release the drug. The composition for rectal or vaginal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the cyclohexylamine compound is dispersed homogeneously therein by stirring. The molten homogeneous mixture is then poured into convenient sized molds, allowed to cool and thereby solidify.

The disclosed composition intended for topical administration may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration.

Transdermal administration includes percutaneous absorption of the composition through the skin. Transdermal formulations include patches, iontophoresis devices, ointments, creams, gels, salves and the like.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet

EXAMPLES

Example 1

Expression and Purification of the Bifunctional Molecule 2D-NBP8

To create the expression plasmid p2D-NBP8-PDI, DNA fragments encoding 2D, the 35-mer linker $(GGGGS)_7$ (SEQ ID NO:34), and NBP8 (SEQ NO:12) were linked together by three-step overlapping PCR. Firstly, the 2D (with 6-his tag), L35 and NBP8 DNA fragments were generated by overlapping PCR using the corresponding primer pairs as depicted in Table 1. Secondly, the DNA fragments coding for L35 and NBP8 were linked by overlapping PCR with the primers FL35 and RNBP8. Thirdly, the two DNA fragments encoding 2D and L35-NBP8 were linked by overlapping PCR with the DNA fragment 2D and the primers F2Dhis and RNBP8. Finally, the amplified DNA fragment coding for NBP8-L35-T20 was digested by BamHI and EcoRI and inserted into the expression vector pGEX-6p-1 to generate the p2D-NBP8 plasmid. In order to prevent the formation of the inclusion bodies in *E. coli*, the protein disulfide isomerase (PDI) DNA sequence (aa18-508) with a precision protease site (called ppase site) was inserted in the N terminus into the EcoR I and Xho I sites located at the C terminus of His-2D-NBP8 gene in the plasmid p2D-NBP8 to extend the GST-his-2D-NBP8 reading frame and resulted in the generation of chimeric GST-his-2D-NBP8-ppase-PDI. This plasmid was called p2D-NBP8-PDI. These sequences were confirmed by DNA sequencing.

TABLE 1

Primers used for constructing the expression vector, pTLT-1

| DNA fragment encoding | | Primer Sequence (5' to 3')* |
|---|---|---|
| 2D | F2Dhis | CGCGGATCCCATCACCATCACCATCATAAGAAAGTGGTGCTG (SEQ ID NO: 27) |
| | R2D | CACTTCCTCCTCCTCCTATGCTGGAGGCCTTCTGGAA (SEQ ID NO: 28) |

TABLE 1-continued

Primers used for constructing the expression vector, pTLT-1

| DNA fragment encoding | Primer | Sequence (5' to 3')* |
|---|---|---|
| 35-mer linker | FL35 | GGAGGAGGAGGAAGTGGCGGCGGCGGCTCGGGTGGTGG TGGTTCTGGAGGTGGCGGTAGCGGAGGTGGAGGTAGTGG AGGC (SEQ ID NO: 29) |
| | RL35 | GCTACCTCCGCCTCCCGAACCTCCGCCTCCACTACCTCCA CCTCCGCTACCGCCACCTCCAGAACCACCACCACCCGAG (SEQ ID NO: 30) |
| NBP8 | FNBP8 | GAGGCGGAGGTAGCACGACCTGGGAAGCATGGGACAGAG CTATTGCTGAATACGCAGCTAGGATAGAAGCTTTACTCAGA GCTTTA (SEQ ID NO: 31) |
| | RNBP8 | CGGAGATCTCTATAATTCC<u>CTTAAG</u>GCTGCTTCATTCTTTTC TTGCTGTTCTTGTAAAGCTCTGAGTAAAGCTTCTATCC (SEQ ID NO: 32) |

*The sequences underlined are restriction enzyme sites used for clone gene into vector pGEX-6p-1.

To express the 2D-NBP8 fusion protein, E. coli strain Rosetta 2 (DE3) pLysS (NOVAGEN®) was transformed with p2D-NBP8-PDI, cultured at 37° C. to $OD_{600}$=0.4, then induced at 16-22° C. for 8-12 hr. The cells were harvested and lysed by sonication in presence of protease inhibitor mixture (Roche). After centrifugation, supernatant containing the GST-his-2D-NBP8-PDI fusion protein were collected. The protein was then purified with Glutathione-Sepharose 4B affinity columns and cleaved with PRESCISSION™ Protease (GE Healthcare) to release the bifunctional proteins from the GST and PDI. The bifunctional proteins were then purified by HIS-BIND® Purification Kit (NOVAGEN®) and fast protein liquid chromatography (FPLC) and analyzed by SDS-PAGE.

The originally designed bifunctional protein consisted of a 185-mer of 2D (KKVVLGKKGDTVELTCTASQKKSIQF-HWKNSNQIKILGNQGSFLTKGPSKLNDRADSR RSL-WDQGNFPLIIKNLKIEDSDTYICEVEDQ-KEEVQLLVFGLTANSDTHLLQGQSLTLTL ESPPGSSPSVQCRSPRGKNIQGGKTLS-VSQLELQDSGTWTCTVLQNQKKVEFKIDIVV LAFQKASSI; SEQ ID NO:33), a 35-mer of linker [(GGGGS)$_7$; SEQ ID NO:34)] and a 38-mer of NBP8 (TTWEAWDRAIAEYAARIEALL-RALQEQQEKNEAALREL; SEQ ID NO:12). Sequencing the resultant vectors indicated that eleven extra amino acid residues (GPLGSHHHHHH; SEQ ID NO:35) at the N-terminus and had eight extra amino acid residues (EFLEVLFQ; SEQ ID NO:36) at the C-termini. The purified bifunctional protein demonstrated a molecular weight of about 30 kD by SDS-PAGE (FIG. 6).

Example 2

Characterization of the Bifunctional Molecule 2D-NBP8

The recombinant bifunctional protein 2D-NBP8 was analyzed by SDS-PAGE and western blotting as previously described (Papanikolopoulou, K., et al. (2004) J. Biol. Chem. 279, 8991-8998). Briefly, 5 μl/well of 100 μM 2D or 2D-NBP8 was mixed with 4×SDS sample buffer (Novagen). The sample was boiled for 5 min or kept at room temperature (RT) before loading onto a 10-20% Tricine-Glycine gel (Invitrogen). The electrophoresis was conducted in SDS-PAGE running buffer with 125V constant voltage at 4° C. The gels were stained with SimplyBlue SafeStain (Invitrogen). In western blot the anti-human CD4 polyclonal antibody (Immuno #7301) and anti-NBP8 polyclonal antibody were used. As expected, the results showed 2D-NBP8 had a molecular weight of about 30 KD and could be detected by both specific antibodies. (FIG. 6)

Figure 8:
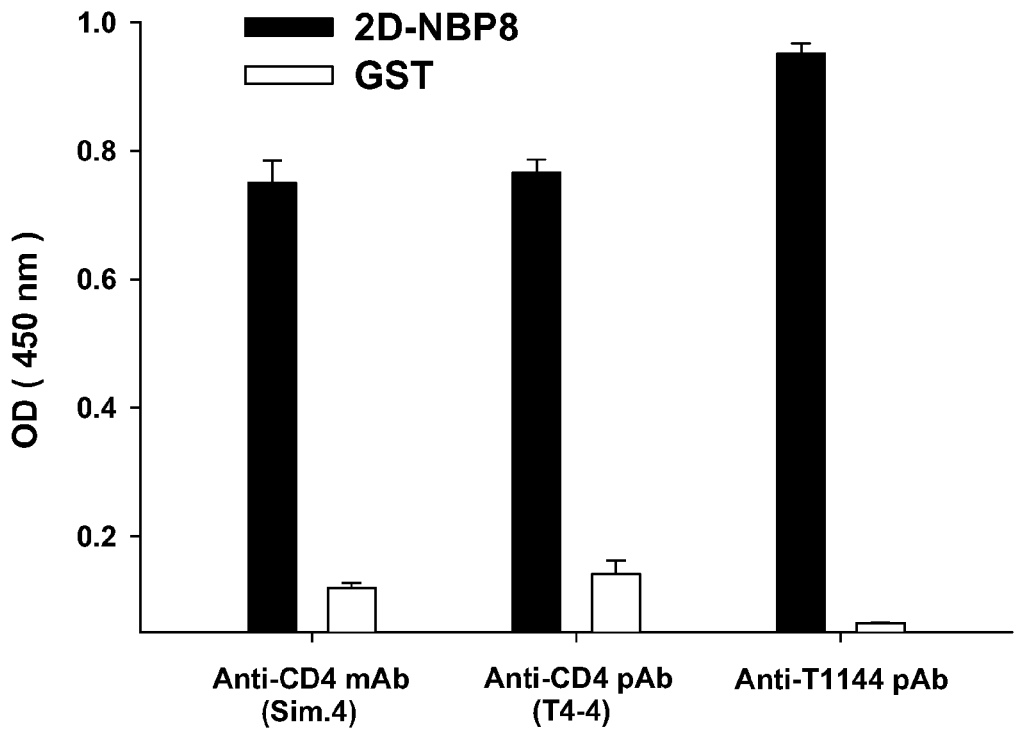
FIG. 8 depicts the biological character of the 2D-NBP8. Polyclonal antibodies (T4-4), conformation-dependent Sim.4 monoclonal antibody against CD4 and polyclonal antibodies against NBP8 were used to detect bound recombinant 2D-NBP8 molecule.

The recombinant bifunctional protein 2D-NBP8 was analyzed by ELISA as previously described (Jiang, S. et al. 1998. J. Virol. 72:10213-10217). Briefly, the 2D and 2D-NBP8 was coated to a 96-well polystyrene plate (Costar) (10 μg/ml in 0.1M Tris-Hcl, pH 8.8) and blocked with 2% non-fat milk in PBS. The plate was then incubated with polyclonal antibodies against CD4 (T4-4), conformation-dependent monoclonal antibody against CD4 (Sim.4) and anti-NBP8 polyclonal antibody for 60 min and the horseradish peroxidase (HRP) secondary antibodies (ZYMED Laboratories) were added. The plate was washed with the washing buffer (PBS containing 0.01% Tween 20) for 5 times. The substrate 3,3',5,5'-tetramethylbenzidine (TMB) (Sigma) was added sequentially. Absorbance at 450 nm (A450) was measured using an ELISA reader (Ultra 384, Tecan). As expected, the results showed soluble 2D-NBP8 could be detected by all the specific antibodies. (FIGS. 7-8)

Example 3

Binding of 2D-NBP8 to gp120 and NHR as Shown by ELISA

Figure 9:
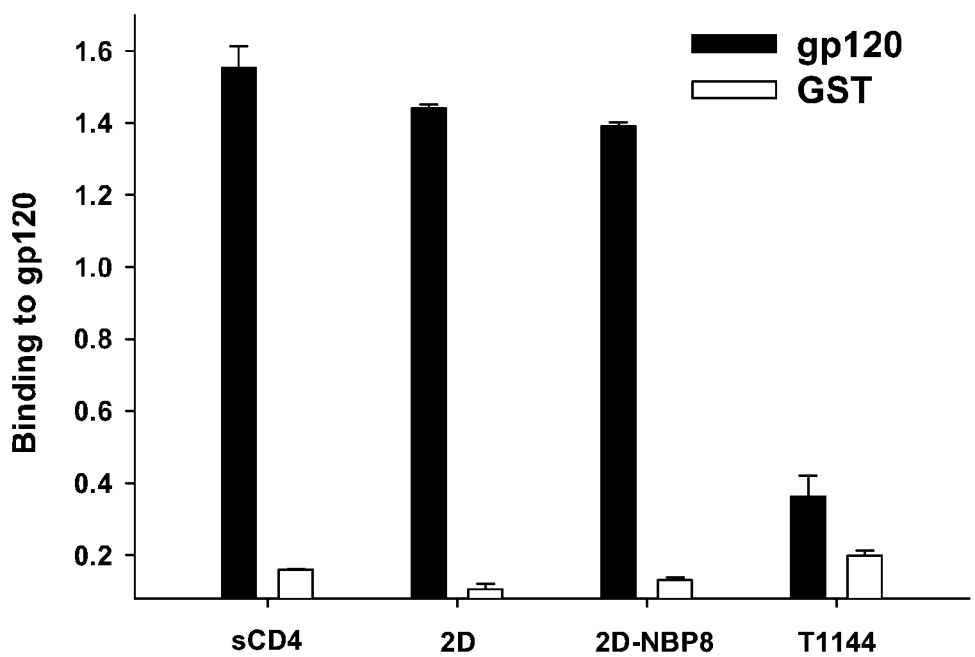
FIG. 9 depicts the binding activity of 2D and 2D-NBP8 to recombinant gp120.
Figure 10:
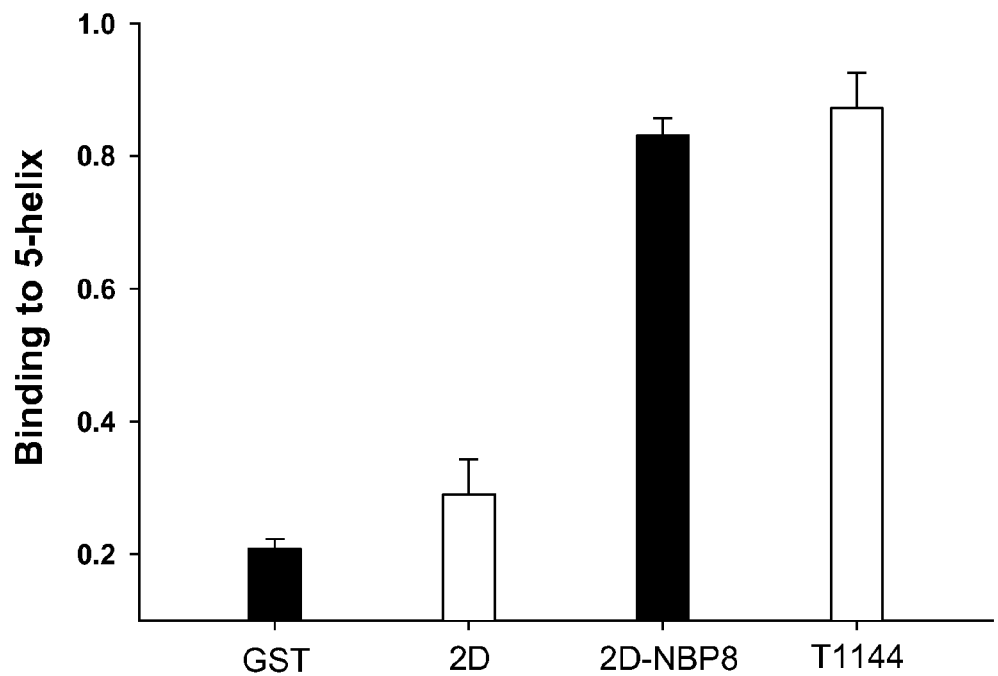
FIG. 10 depicts the binding activity of 2D and 2D-NBP8 to 5-helix.

The binding of 2D-NBP8 to gp120 and NHR was detected by ELISA as previously described (Huang J H et al. 2006. FEBS Letter. 580:4807-14). Briefly, the testing proteins were coated to a 96-well polystyrene plate (10 μg/ml in 0.1M Tris-Hcl, pH 8.8) and blocked with 2% non-fat milk in PBS. The plate was then incubated with biotinylated gp120 or 5-helix 2 μg/ml in PBS) at 37° C. for 30 min. The plate was washed with the washing buffer (PBS containing 0.01% Tween 20) five times. Then, the plate was incubated with horseradish peroxidase (HRP) labeled with streptavidin (SA-HRP) (ZYMED Laboratories) and the plate was washed five times. The substrate TMB was then added and absorbance at 450 nm (A450) was measured using an ELISA reader. As shown in FIGS. 9-10, functional binding was detected between 2D-NBP8 and gp120 and between 2D-NBP8 and 5-helix (a mimic NHR molecule).

Example 4

Figure 11:
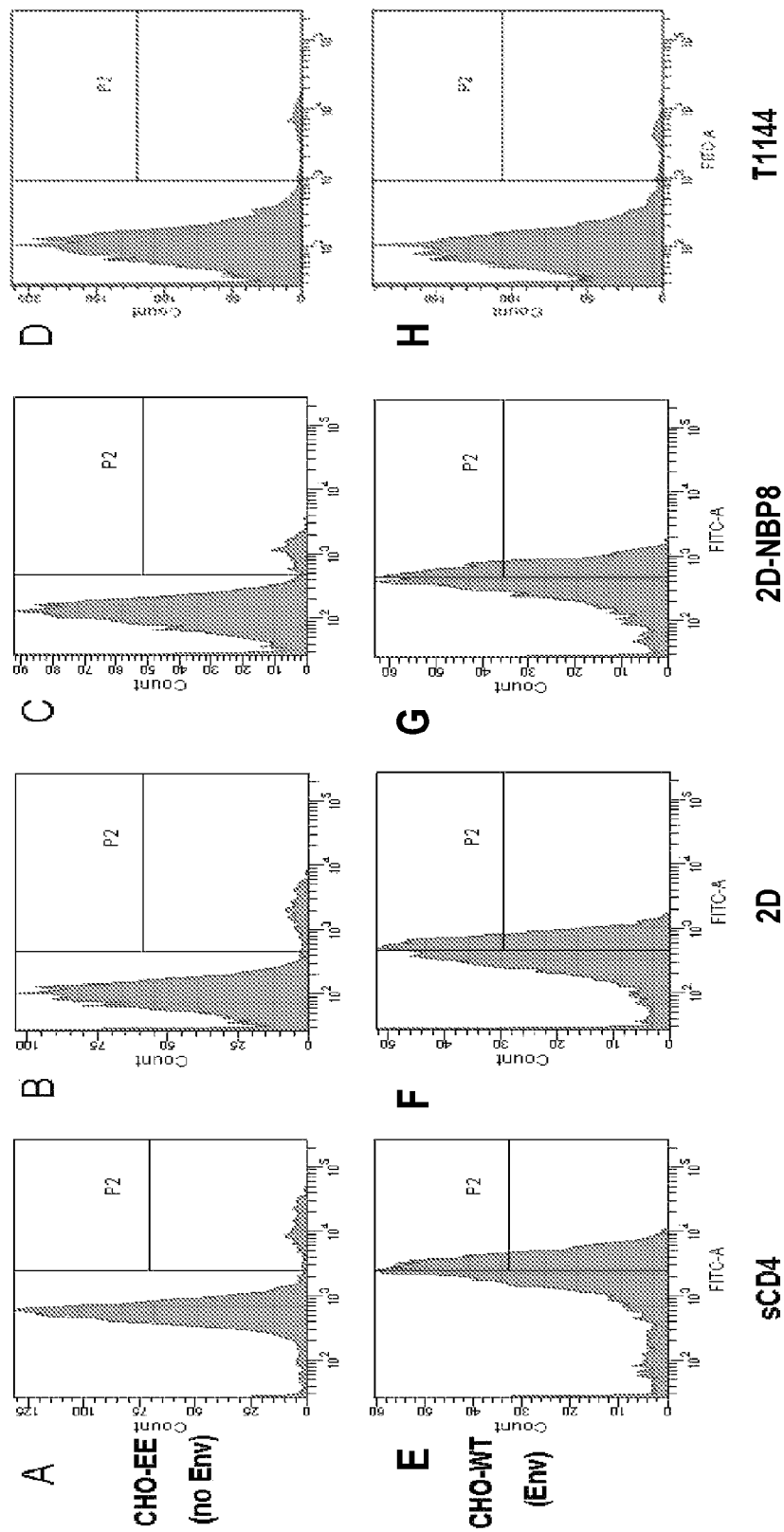
FIG. 11 depicts the functional activity of the 2D and 2D-NBP8. 2D (FIGS. 11B and 11F) and 2D-NBP8 (FIGS. 11C and 11G) both have the binding ability to wild type gp120/gp41 on the surface CHO-WT (FIGS. 11E-H) as detected by flow cytometric analysis. CHO-EE (FIGS. 11A-D) expressing no gp120/gp41 were included as control.

Binding of 2D-NBP8 to Natural gp120/gp41 on Cell Surface as Detected by Flow Cytometry The binding of 2D-NBP8 to natural gp120/gp41 on cell surface was detected by flow cytometry as previously described (Jiang S. et al.). Briefly, CHO-EE (no Env) and CHO-WT (has Env) were detached and washed with wash buffer (PBS containing 5% GBS) three times. Then they were incubated with the testing protein for 1 hr at 4° C. After three washes, anti-human CD4 polyclonal antibody (Immuno #7301) and anti-NBP8 polyclonal antibody were added for 1 hr at 4° C. After three washes, FITC-conjugated anti-rabbit or mouse antibody were added and incubated for 1 hr at 4° C. After at least three washings, the cells were examined by flow cytometry and the fluorescence intensity was recorded by FACSCALIBUR™ (Becton Dickinson). As shown in FIG. 11, 2D-NBP8 can functionally bind to the native HIV Env expressed on the effector cells as sCD4.

Example 5

Binding Affinity of 2D-NBP8 to gp120 as Neasured by SPR

Figure 12:
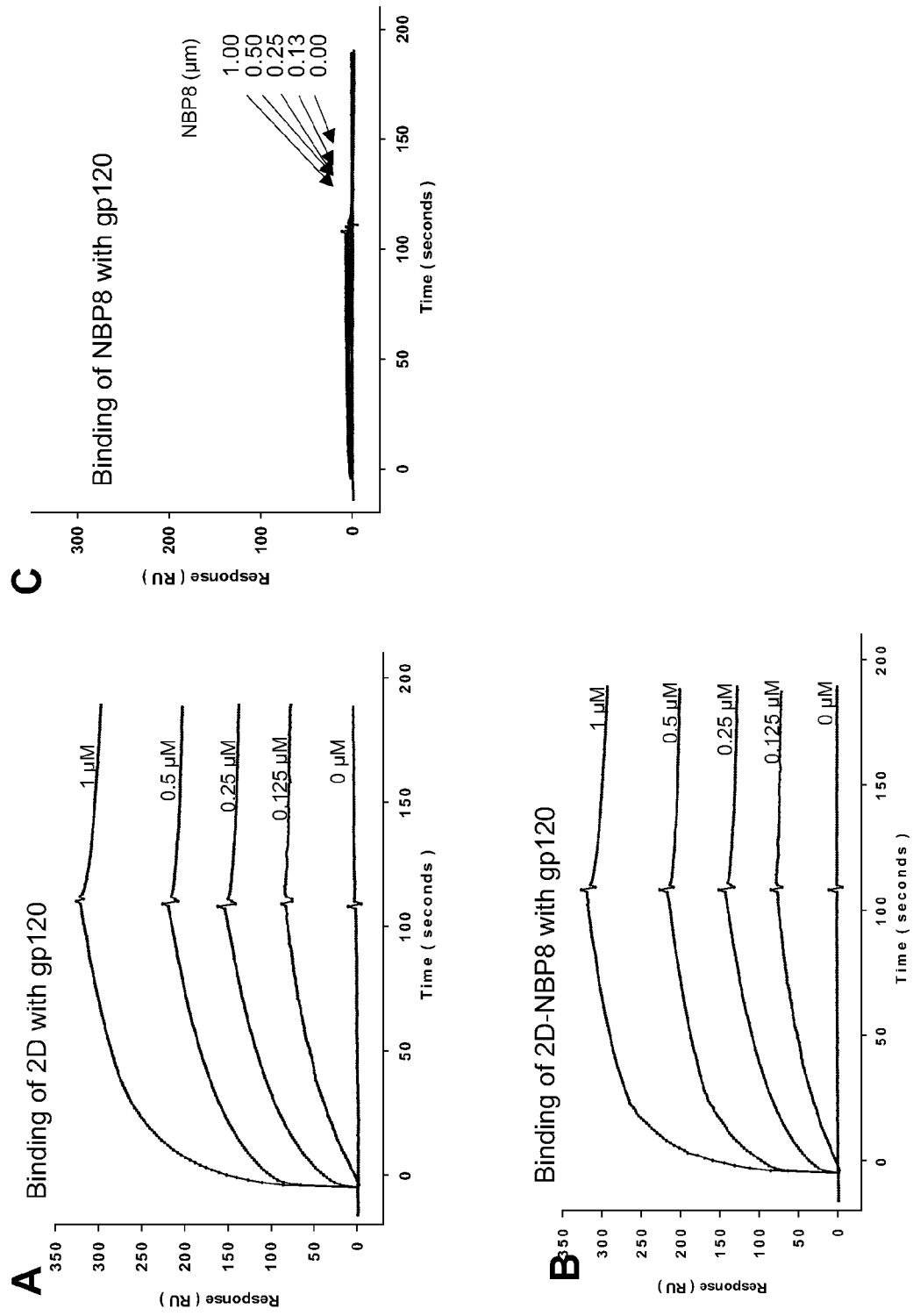
FIG. 12 depicts the binding affinity of 2D and 2D-NBP8 by surface plasmon resonance (SPR) analysis.

The binding affinity of 2D-NBP8 to gp120 was measured by surface plasmon resonance (SPR) using BIACORE® 3000 system (Pharmacia), following the Biomolecular Interaction Analysis (BIA) Technology Manual as previously described (Lu, L et al. Journal of Biological Chemistry 283: 16723-16731). Briefly, gp120 (100 μg/ml) was immobilized onto the CM5 sensor chip by amine coupling, and the unreacted sites were blocked with ethanolamine. The association reaction was initiated by injecting 35 μl protein sample at a flow rate of 5 μl/min. The dissociation reaction was done by washing with running buffer (10 mM HEPES pH7.4 containing 0.15M NaCl, 3.4 mM EDTA and 0.005% v/v Surfactant) for at least 2 min. As shown in FIG. 12 and Table 2, the recombinant 2D-NBP8 protein has high affinity to gp120 (KD $1.9e10^{-8}$).

TABLE 2

| Protein | | Ka $M^{-1}S^{-1}$ | Kd $S^{-1}$ | KA $M^{-1}$ | KD M |
|---|---|---|---|---|---|
| GP120+ | T1144 | $2.8e^3$ | $5.2e^{-3}$ | $5.4e^5$ | $1.8e^{-6}$ |
| | 2D | $2.2e^4$ | $4.7e^{-4}$ | $4.8e^7$ | $2.1e^{-8}$ |
| | 2D-NBP8 | $2.5e^4$ | $4.8e^{-4}$ | $5.2e^7$ | $1.9e^{-8}$ |

Example 6

2D-NBP8 Inhibits 6-Helix Bundle Formation

The ability of 2D-NBP8 to prevent 6-HB formation was determined by ELISA and FN-PAGE using a fluorescence C34-FAM probe as previously described (Liu S W et al. 2005 JBC 280:12, 11259-11273). Briefly, a testing peptide was pre-incubated with equal amount of N36 at 37 C for 30 min, followed by the addition of C34-biotin (0.5 μM). The mixture was added to a 96-well polystyrene plate coated with mAb NC-1 IgG (2 μg/ml in 0.1M Tris, pH 8.8) and blocked with 2% non-fat milk in PBS. The plate was then incubated for 30 min and SA-HRP was added. The plate was washed with the washing buffer (PBS containing 0.01% Tween 20) six times to remove any unbound peptide. The substrate TMB was added and the absorbance at 450 nm (A450) was measured using an ELISA reader. The percent inhibition of 6-HB formation and the $IC_{50}$ values were calculated using the CALCUSYN™ software.

In the FN-PAGE assay, a testing peptide was preincubated with an equal amount of N36 at 37° C. for 30 min, followed by the addition of C34-FAM at 37° C. for 30 min. And then the mixtures were added into Tris-glycine native sample buffer (Invitrogen). The samples (20 μl) were then loaded onto Tris-glycine gels (18%), which were run under 120 V constant voltage at room temperature for 1 hrs. The gels were stained visualized with the FLUORCHEM® 8800 Imaging System (Alpha Innotech Corp.) using a transillumination UV light source with excitation wavelength at 520 nm and then stained with Coomassie blue.

Figure 13:
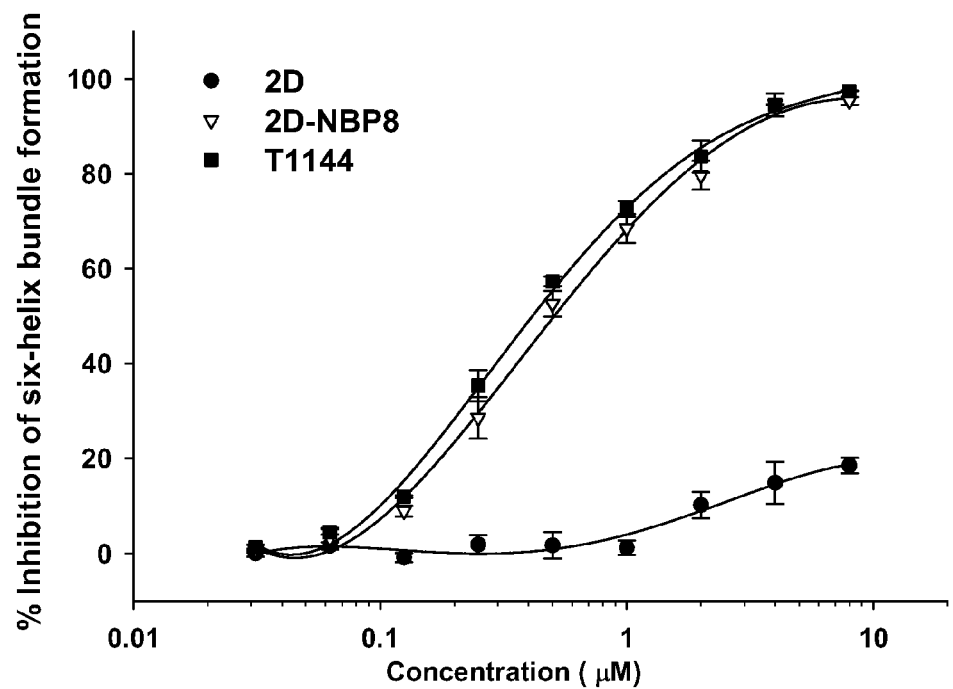
FIG. 13 depicts the inhibitory effect of 2D-NBP8 on 6-HB formation in the ELISA assay.
Figure 14:
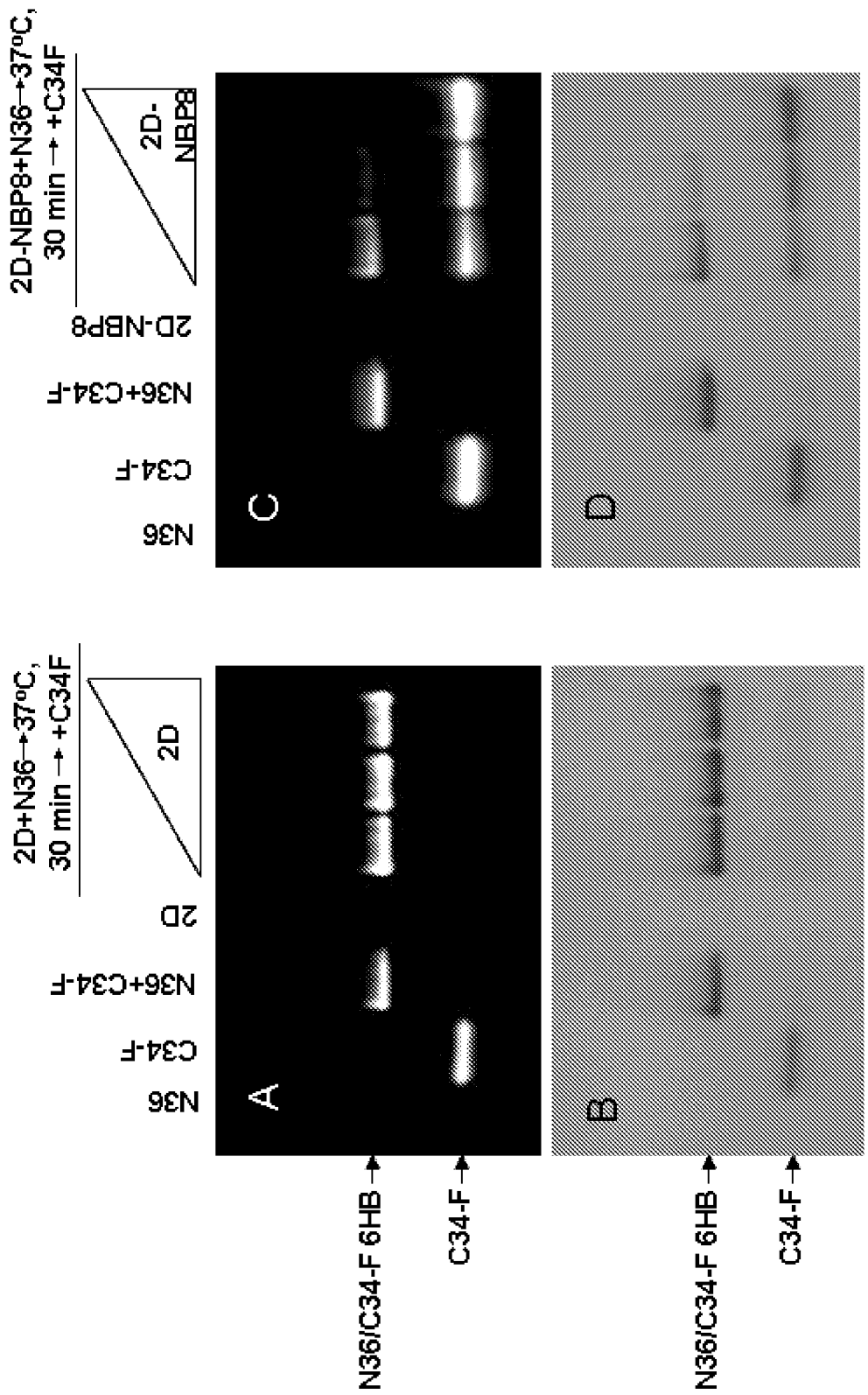
FIG. 14 depicts the inhibitory effect of 2D-NBP8 on 6-HB formation in the Fluorescence Native-PAGE assay (FN- PAGE).

As shown in FIG. 13, 2D-NBP8 could strongly inhibit N36/C34 6-HB formation like T1144, while 2D was ineffective in blocking the 6-HB formation. The result was further confirmed in FN-PAGE assay. With an increase in concentration (from 1 μM to 10 μM), 2D-NBP8 was able to prevent C34-FAM/N36 6-HB formation completely (FIG. 14).

Example 7

Inhibitory Activity of 2D-NBP8 on HIV-1-Mediated Cell-Cell Fusion and HIV-1 Replication HIV-1-mediated cell-cell fusion was determined by a dye transfer assay (Lu H et al. J Virol Methods 107:155-161, 2003.) using Calcein AM-labeled HIV-1IIIB chronically infected H9 (H9/HIV-1 IIIB) cells as effector cells and MT-2 cells as target cells. The percent inhibition of cell-cell fusion by the chimeras was calculated, and 50% inhibitory concentration (IC50) was calculated using the CalcuSyn software. As shown in Table 3, 2D-NBP8 was highly effective in inhibiting HIV-1-mediated cell-cell fusion with IC50 (19.03 nM) at low nM level.

Figure 15:
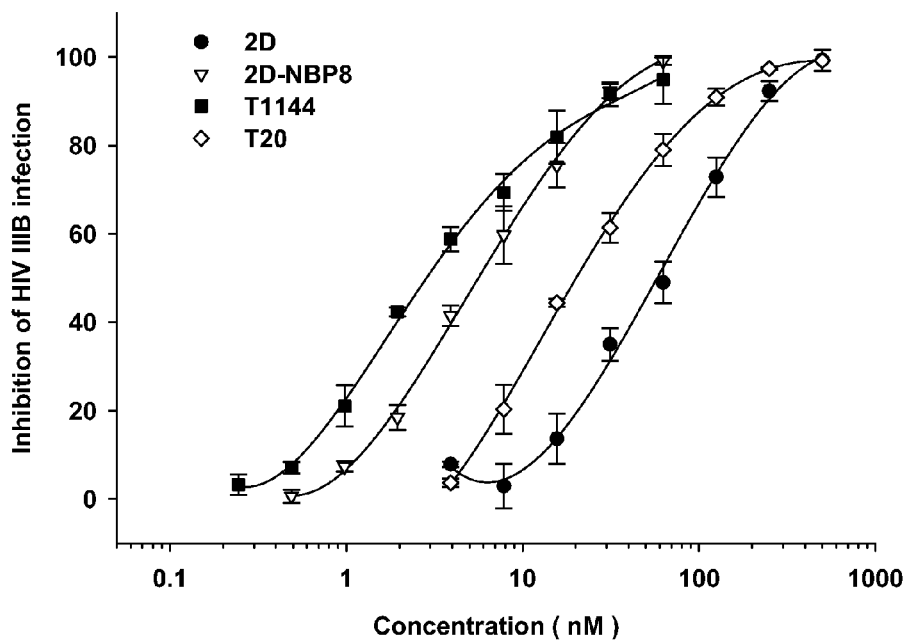
FIG. 15 depicts the inhibition by 2D and 2D-NBP8 of infection by a laboratory-adapted HIV-1 IIIB strain (subtype B, X4) in MT-2 cells as determined by p24 assay.

The inhibitory activity of the bifunctional molecule on HIV-1 IIIB infection was determined by ELISA for p24 production (Jiang S et al. J Exp Med 174:1557-1563, 1991). Briefly, MT-2 cells were infected with HIV-1IIIB at 100 $TCID_{50}$ (50% tissue culture infective dose) in RPMI 1640 medium containing 10% FBS in the presence or absence of an antigen specific antiserum or IgG antibody in serial 2-fold dilutions at 37° C. overnight. The culture supernatants were then removed and fresh media were added. On day 4 post-infection, the culture supernatants were collected and mixed with equal volumes of 5% TRITON™ X-100 for the detection in the p24 protein ELISA. 2D-NBP8 was also highly potent in inhibiting HIV-1 IIIB infection with $IC_{50}$ at 5.64 nM, more than 3-fold better than T20 (FIG. 15 and Table 3).

Figure 16:
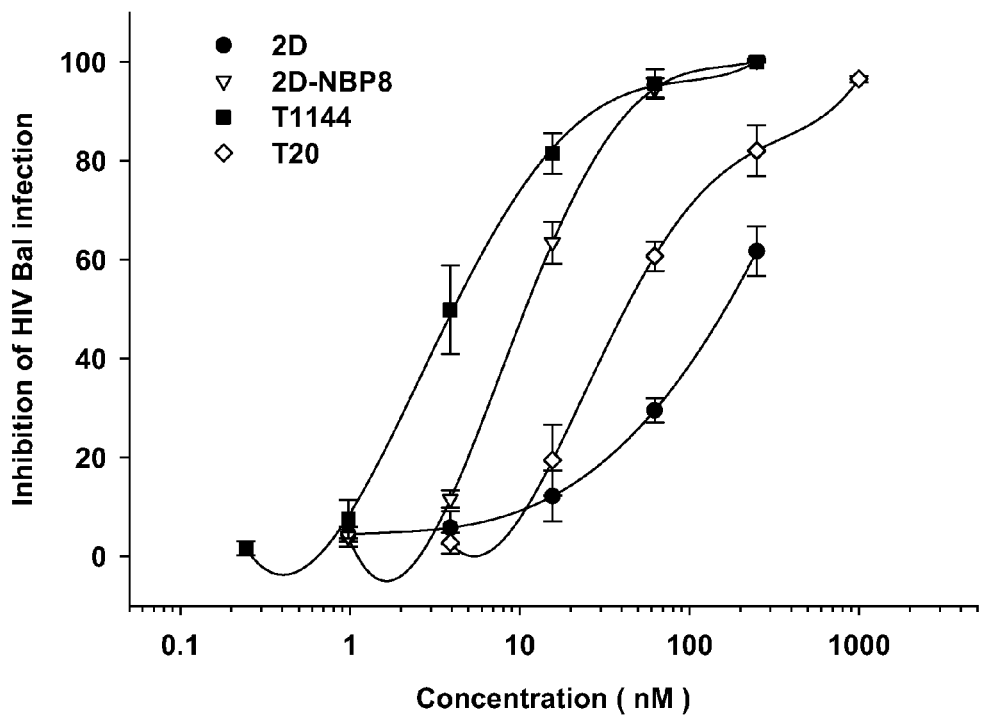
FIG. 16 depicts the inhibition by 2D and 2D-NBP8 of infection by a HIV-1 Bal strain (subtype B, R5) in M7 cells as determined by luciferase assay.

For inhibition of infection by the M-tropic HIV-1 strain Bal (subtype B, R5), 100 μl of TZM-bl cells ($1 \times 10^5$/ml) were pre-cultured overnight and infected with Bal at 100 $TCID_{50}$ in the presence or absence of the test peptide overnight. The cells were harvested and lysed on the fourth day post-infection with 50 μl of lysing reagent. The luciferase activity was analyzed using a luciferase kit (Promega) and a luminometer (Ultra 386, Tecan) according to the manufacturer's instruction. The percent inhibition of luciferase activity was calculated. As shown in FIG. 16 and Table 3, 2D-NBP8 was also highly potent in inhibiting HIV-1 IIIB infection with $IC_{50}$ at 10.78 nM, much better than T20.

The inhibitory activity of the bifunctional molecule on infection by primary HIV-1 isolates, 92US657 (B, R5), 94UG103 (A, X4R5), 93MW959 (C, R5), RU570 (G, R5) and 92TH009 (E/A, R5) was determined (Jiang S et al. Antimicrob Agents Chemother 48:4349-4359, 2004). Briefly, peripheral blood mononuclear cells (PBMCs) were isolated from the blood of healthy donors using a standard density gradient (Histopaque-1077, Sigma) centrifugation. After incubation at 37° C. for 2 hr, the nonadherent cells were collected and resuspended at 5×105/ml in RPMI 1640 medium containing 10% FBS, 5 µg of phytohemagglutinin (PHA)/ml, and 100 U of IL-2/ml, followed by incubation at 37° C. for 3 days. The PHA-stimulated cells were infected with the corresponding primary HIV-1 isolates at a multiplicity of infection (MOI) of 0.01 in the absence or presence of antisera at a serial 2-fold dilution. The supernatants were collected 7 days post-infection and tested for p24 antigen by ELISA as described above. The $IC_{50}$ was calculated using the CALCUSYN™ software as described above. As shown in Table 3, 2D-NBP8 significantly inhibited infection by all the primary HIV-1 isolates in with $IC_{50}$ at low nM level.

shown in the Table 4, both 2D-NBP1 and 2D-FBP1 were effective in inhibiting HIV-1-mediated cell-cell fusion and HIV-1 replication, suggesting that the NHR-binding peptide and the fusion peptide-binding peptide linked to 2D or CD4 molecule retain their anti-HIV-1 activity.

TABLE 4

Inhibitory activity of the recombinant proteins on HIV-1-mediated cell-cell fusion and HIV-1 replication

| | $EC_{50}$ (nM) for inhibiting infection by | | |
|---|---|---|---|
| | Bal (B, R5) | IIIB (B, X4) | Cell-cell fusion |
| 2D-NBP1 | 192.2 | 291.8 | 289.4 |
| 2D-FBP1 | 67.87 | 205.2 | 111.3 |

TABLE 3

Inhibitory activity of the peptides and recombinant proteins on HIV-1-mediated cell-cell fusion and HIV-1 replication

| | 2D | | 2D-NBP8 | | T20 | | T1144 | |
|---|---|---|---|---|---|---|---|---|
| Concentration (nM) | $IC_{50}$ | $IC_{90}$ | $IC_{50}$ | $IC_{90}$ | $IC_{50}$ | $IC_{90}$ | $IC_{50}$ | $IC_{90}$ |
| HIV-1 IIIB-mediated cell fusion | 97.83 | 137.18 | 19.03 | 46.51 | 20.15 | 41.71 | 5.89 | 15.26 |
| HIV-1 replication | | | | | | | | |
| IIIB (B, X4) | 56.80 | 246.02 | 5.64 | 28.79 | 17.26 | 117.21 | 2.13 | 35.23 |
| Bal (B, R5) | 170.20 | >250 | 10.78 | 44.35 | 43.35 | >250 | 4.03 | 28.11 |
| 92US657 (B, R5)* | >250 | >250 | 17.17 | 51.85 | 56.07 | 223.92 | ND | ND |
| 94UG103 (A, X4R5)* | >250 | >250 | 14.53 | 59.83 | 6.67 | 29.43 | ND | ND |
| 93MW959 (C, R5)* | >250 | >250 | 18.93 | 48.86 | 4.70 | 18.76 | ND | ND |
| RU570 (G, R5)* | >250 | >250 | 55.58 | 146.39 | 44.08 | 109.66 | ND | ND |
| 92TH009 (E/A, R5)* | 25.30 | 113.69 | 17.50 | 71.93 | 1.43 | 7.99 | ND | ND |

*Primary HIV-1 isolates

Example 8

Inactivation of HIV Isolates by 2D-NBP8

Figure 17:
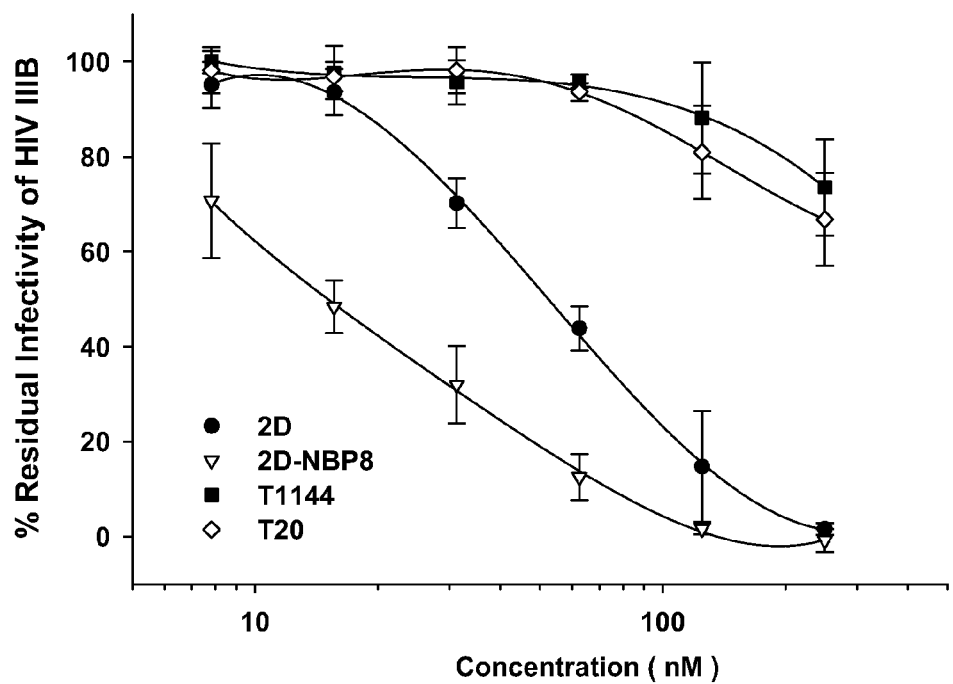
FIG. 17 depicts the virus inactivation activity of 2D, 2D-NBP8, NBP8 and T20 by a laboratory-adapted HIV-1 IIIB strain (subtype B, X4) in MT-2 cells as determined by p24 assay.
Figure 18:
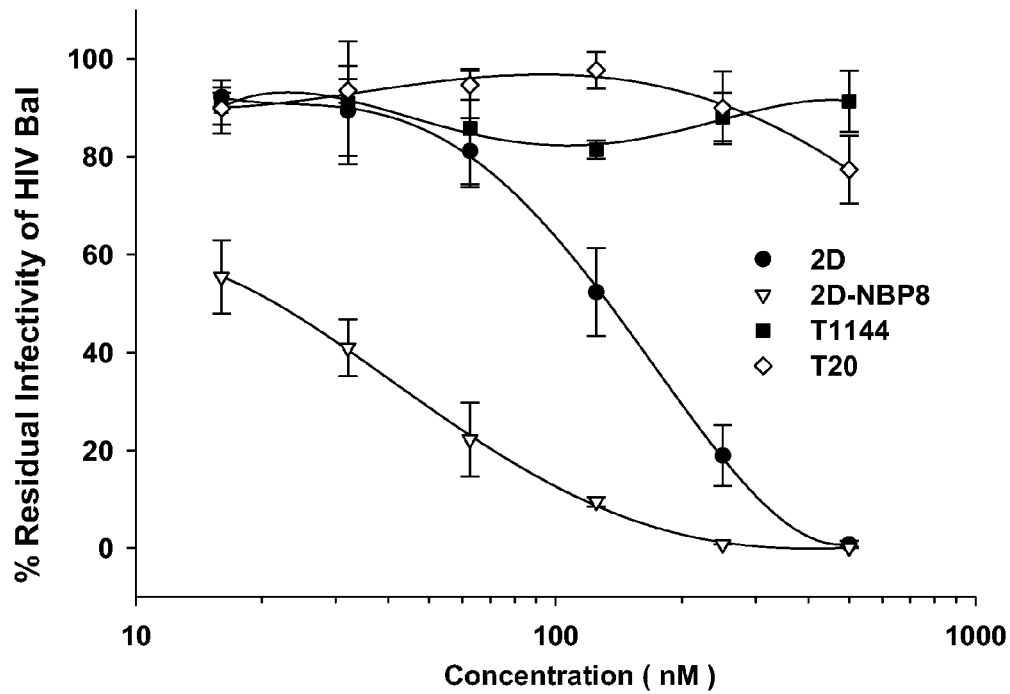
FIG. 18 depicts the virus inactivation activity of 2D, 2D-NBP8, NBP8 and T20 by a HIV-1 Bal strain (subtype B, R5) in M7 cells as determined by luciferase assay.

Virus inactivation by 2D-NBP8 was determined by ELISA for p24 production or luciferase kit. Briefly, HIV-1 isolate (500 $TCID_{50}$/ml) was added to 100 µl of the samples with different concentration and incubate on 4° C. for 1 hour. Then, PEG 6000 was added to the final concentration of 3% and centrifuge on a microfuge at 15,000 rpm for 30 min. The supernatants were removed, and the pellet was washed with PBS and resuspended to 100 µl. MT-2 or TZM-bl cells ($1 \times 10^5$/ml) were added at 100 µl/well, and cultured at 37° C. for 3 days. p24 production in MT-2 or luciferase activity was determined according to kit manufacturer' instruction. Results shown in FIG. 17-18 indicate that 2D-NBP8 in a dose-dependent manner rapidly inactivates HIV-1 IIIB, an X4 virus and HIV-1 Bal, an R5 virus. In contrast, there were no significant effects on virus within a concentration range tested in the T20 and T1144 group.

Example 9

Inhibitory Activity of the 2D-NBP1 and 2D-FBP1 on HIV-1-Mediated Cell-Cell Fusion and HIV-1 Replication 2D-NBP8

The inhibitory activity of the 2D-NBP1 and 2D-FBP1 on HIV-1-mediated cell-cell fusion and infection by the HIV-1 strains Bal and IIIB were determined as described above. As Example 10

Inactivation of HIV Isolates by 2D-NBP1 and 2D-FBP1

Inactivation of the cell-free HIV-1 strains Bal and IIIB by 2D-NBP1 and 2D-FBP1 was detected as described above. As shown in the Table 5, both 2D-NBP1 and 2D-FBP1 could significantly inactivate the viruses with $EC_{50}$ in the range of 80-300 nM, confirming that the recombinant proteins consisting of 2D or CD4 fused with the NHR-binding peptide and the fusion peptide-binding peptide linked to molecule are effective HIV-1 inactivators.

TABLE 5

Inactivation of cell-free HIV-1 R5 and X4 strains

| | $EC_{50}$ (nM) for inhibiting infection by | |
|---|---|---|
| | Bal (B, R5) | IIIB (B, X4) |
| 2D-NBP1 | 299.12 | 173.46 |
| 2D-FBP1 | 169.21 | 81.25 |

Example 11

The Potential Mechanism of Virus Inhibition by 2D-NBP8

2D-NBP8 can destabilize and inactivate the 2D-activated envelope glycoprotein intermediate through interacting with exposed N-HR domain. To measure the effects of 2D-NBP8 on HIV-1 envelope glycoprotein, an ELISA-based system that utilizes live cells as a platform for expression of membrane-bound trimeric envelope glycoprotein complexes was used as previously described (Haim H et al. Plos pathogens. 5:4, 1-13, 2009). Briefly, CHO-WT cells steadily expressing HIV-1 Env were seeded in 96-well plates ($5 \times 10^4$ per well) and cultured at 37° C. Two days later, the cells were washed twice with blocking buffer (35 mg/ml BSA, 10 mg/ml non-fat dry milk, 1.8 mM $CaCl_2$, 1 mM $MgCl_2$, 25 mM Tris, pH 7.5 and 140 mM NaCl). For pulse activation experiments, the cells were incubated with 2D (2.5 µM) or 2D-NBP8 (2.5 µM) suspended in blocking buffer for three minutes, washed three times with blocking buffer and incubated for different time periods with C34-biotin (at 2 µM for 30 minutes). To study the temperature dependence of HR1 groove exposure, the 2D-pulsed cells were incubated at the requisite temperature for different lengths of time; the cells were subsequently returned to room temperature for incubation with C34-biotin. Cells were then washed four times with blocking buffer and four times with washing buffer (140 mM NaCl, 1.8 mM $CaCl_2$, 1 mM $MgCl_2$ and 20 mM Tris, pH 7.5). SA-HRP was then incubated with the samples for 45 minutes at RT. Cells were washed 5 times with blocking buffer and five times with washing buffer. HRP enzyme activity was determined after the addition of 33 µl per well of a 1:1 mix of WESTERN LIGHTNING® oxidizing and luminol reagents (Perkin Elmer Life Sciences) supplemented with 150 mM NaCl. Light emission was measured.

Using above method, Haim et al. (*PLoS. Pathog.* 5:e1000360, 2009) found the sCD4 and CD4-mimetic compounds significantly enhanced the binding of the C34 to the HIV-1 envelope glycoprotein, which suggested the exposure of the NHR groove (C34 binding site) on Env after the sCD4 pulse. And importantly, their results showed the stability of the sCD4-activated NHR exposed intermediate was closely related to HIV-1 infectivity after activation by sCD4, especially the HIV-1 infection of CD41CCR5$^+$ cells which can be enhanced after sCD4 and CD4-mimetic compounds. As shown in FIG. 19, 2D-NBP8 could significantly destabilize and inactivate the 2D-activated Env fusion intermediate through interacting with exposed NHR groove induced by 2D.

Example 12

Figure 20:
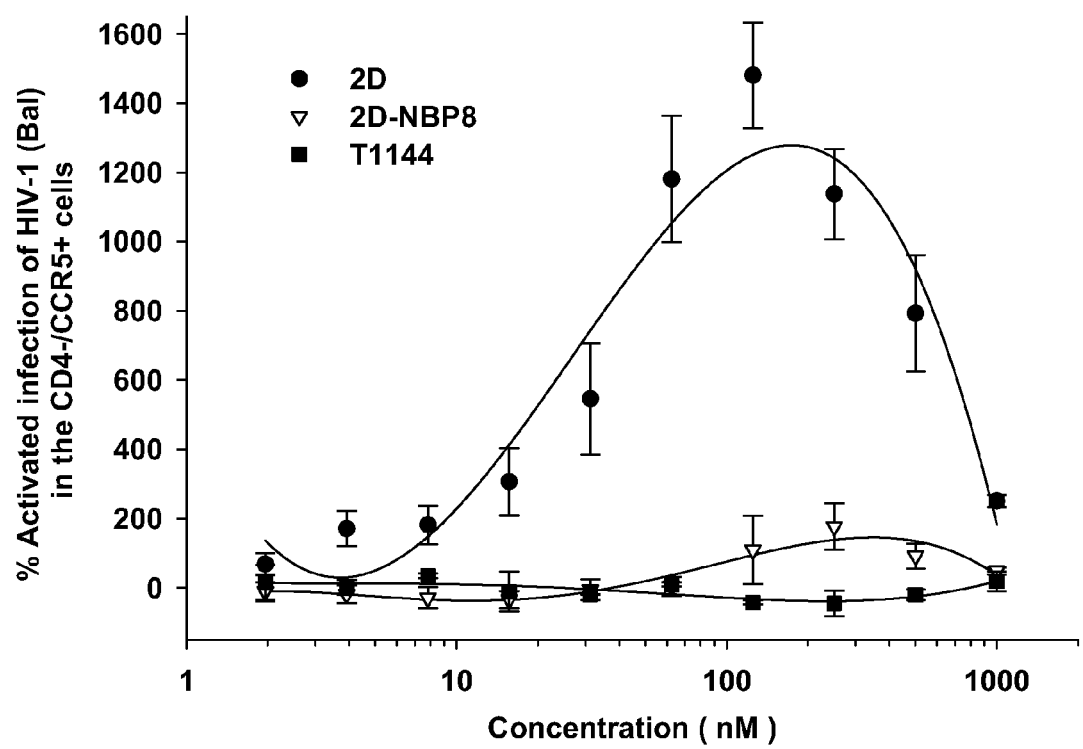
FIG. 20 depicts the inhibition of infectivity of cell-bound virus activated by 2D.

2D-NBP8 can Significantly Reduce the Enhancement Effects of CD4-Related on the HIV-1 Infection of the CD4$^-$/CCR5$^+$ Cells Soluble sCD4 has been shown to modestly enhance HIV-1 infection of CD4$^-$/CCR5$^+$ cells (Haim H et al.). Since 2D-NBP8 contains the D1D2 domain of sCD4, it is necessary to investigate whether 2D-NBP8 could also HIV-1 infection of CD4$^{-1}$/CCR5$^+$ cells using the same method as described by Haim et al. Briefly, Cf2Th-CCR5 cells (NIH ARRRP CN4662) ($6 \times 10^5$ cells per well) and the virus (HIV-1 Bal) were mixed in the presence of different concentrations of 2D and 2D-NBP8 in the culture medium and infectivity was measured three days later. The results showed that 2D enhanced virus infection in some concentration ranges, while 2D-NBP8 did not enhance, but rather significantly suppressed, the enhancement effects of CD4-related on the HIV-1 infection of the CD4$^{-1}$/CCR5$^+$ (FIG. 20).

TABLE 6

Sequences of components of the bifunctional HIV entry inhibitors

| Molecule | SEQ ID NO | Sequence |
|---|---|---|
| 2D-NBP (source of NBP) | | |
| 2D-NBP1 (C46) | 37 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)$_7$WMEWDREINNYTSLIHSLI EESQNQQEKNEQELLELDKWASLWNWF |
| 2D-NBP2 (C38) | 38 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)$_7$TTWMEWDREINNYTSLIH SLIEESQNQQEKNEQELLEL |
| 2D-NBP3 (C36) | 39 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)$_7$WMEWDREINNYTSLIHSLI EESQNQQEKNEQELLEL |
| 2D-NBP4 (C34) | 40 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK |

TABLE 6-continued

Sequences of components of the bifunctional HIV entry inhibitors

| Molecule | SEQ ID NO | Sequence |
|---|---|---|
| | | VEFKIDIVVLAFQKASSI(GGGGS)₇WMEWDREINNYTSLI<br>EESQNQQEKNEQELL |
| 2D-NBP5<br>(C28) | 41 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇WMEWDREINNYTSLIHSLI<br>EESQNQQEK |
| 2D-NBP6<br>(C51) | 42 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇WMEWDREINNYTSLIHSLI<br>EESQNQQEKNEQELLELDKWASLWNWF |
| 2D-NBP7<br>(sifuvirtide) | 43 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇SWETWEREIENYTKQIYKI<br>LEESQEQQDRNEKDLLE |
| 2D-NBP8<br>(T1144) | 44 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇TTWEAWDRAIAEYAARIE<br>ALLRALQEQQEKNEAALREL |
| 2D-NBP9<br>(C35-EK) | 45 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇WEEWDKKIEEYTKKIEELI<br>KKSEEQQKKNEEELKK |
| 2D-NBP10<br>(CP621-652) | 46 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇QIWNNMTWMEWDREINN<br>YTSLIHSLIEESQNQ |
| 2D-NBP11<br>(CP32M) | 47 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇VENETWMEWEREIENYT<br>KLIYKILEESQEQ |
| 2D-NBP12<br>(T1249) | 48 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇WQEWEQKITALLEQAQIQ<br>QEKNEYELQKLDKWASLWEWF |
| 2D-NBP13<br>(PBD-4HR) | 49 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇WMEWDREIEEYTKKIEEY<br>TKKIEEYTKKIEEYTKKI |
| 2D-NBP14<br>(CBD1) | 50 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)₇SLEQIWNNMTWMQWDK |
| 2D-NBP15<br>(T20) | 51 | KKVVLGKKGDTVELTCTASQKKSIQFHWKNSNQIKILGNQGS<br>FLTKGPSKLNDRADSRRSLWDQGNFPLIIKNLKIEDSDTYICE |

TABLE 6-continued

Sequences of components of the bifunctional HIV entry inhibitors

| Molecule | SEQ ID NO | Sequence |
|---|---|---|
| | | VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇YTSLIHSLIEESQNQQEKN EQELLELDKWASLWNWF |

2D-CBP (source of CBP)

| Molecule | SEQ ID NO | Sequence |
|---|---|---|
| 2D-CBP1 (N46) | 52 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇TLTVQARQLLSGIVQQQN NLLRAIEAQQHLLQLTVWGIKQLQARIL |
| 2D-CBP2 (N36) | 53 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇SGIVQQQNNLLRAIEAQQ HLLQLTVWGIKQLQARIL |
| 2D-CBP3 (N34) | 54 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇SGIVQQQNNLLRAIEAQQ HLLQLTVWGIKQLQAR |
| 2D-CBP4 (N51) | 55 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASS(GGGGS)₇QARQLLSGIVQQQNNLLR AIEAQQHLLQLTVWGIKQLQARILAVERYLKQQ |
| 2D-CBP5 (DP-107) | 56 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇NNLLRAIEAQQHLLQLTV WGIKQLQARILAVERYLKDQ |
| 2D-CBP6 (N17) | 57 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇LLQLTVWGIKQLQARIL |
| 2D-CBP7 (N28) | 58 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇IEAQQHLLQLTVWGIKQL QARILAVERY |

2D-FBP (source of FBP)

| Molecule | SEQ ID NO | Sequence |
|---|---|---|
| 2D-FBP1 (VIRIP164) | 59 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇LEAIPCSIPPCVFFNKPFV F |
| 2D-FBP2 (VIRIP165) | 60 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS VQCRSPRGKNIQGGKTLSVSQLELQDSGTWTCTVLQNQKK VEFKIDIVVLAFQKASSI(GGGGS)₇LEAIPCSIPPCVFANKPFV F |
| 2D-FBP3 (VIRIP353) | 61 | KKVVLGKKGDTVELTCTASQKKSIQFHWKNSNQIKILGNQGS FLTKGPSKLNDRADSRRSLWDQGNFPLIIKNLKIEDSDTYICE VEDQKEEVQLLVFGLTANSDTHLLQGQSLTLTLESPPGSSPS |

TABLE 6-continued

Sequences of components of the bifunctional HIV entry inhibitors

| Molecule | SEQ ID NO | Sequence |
|---|---|---|
| | | VQCRSPRGKNIQGGKTLSVSQLELQDSGTWTCTVLQNQKK<br>VEFKIDIVVLAFQKASSI(GGGGS)$_7$LEAIPCSIPPCFLFNKPFVF |
| 2D-FBP4<br>(VIRIP576) | 62 | KKVVLGKKGDTVELTCTASQKKSIQFHWKNSNQIKILGNQGS<br>FLTKGPSKLNDRADSRRSLWDQGNFPLIIKNLKIEDSDTYICE<br>VEDQKEEVQLLVFGLTANSDTHLLQGQSLTLTLESPPGSSPS<br>VQCRSPRGKNIQGGKTLSVSQLELQDSGTWTCTVLQNQKK<br>VEFKIDIVVLAFQKASSI(GGGGS)$_7$LEAIPCSIPPEFLFGKPFVF |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

SEQUENCE LISTING

```
<160> NUMBER OF SEQ ID NOS: 64

<210> SEQ ID NO 1
<211> LENGTH: 36
<212> TYPE: PRT
<213> ORGANISM: Human immunodeficiency virus

<400> SEQUENCE: 1

Ser Gly Ile Val Gln Gln Gln Asn Asn Leu Leu Arg Ala Ile Glu Ala
```

-continued

```
                1               5                  10                  15
Gln Gln His Leu Leu Gln Leu Thr Val Trp Gly Ile Lys Gln Leu Gln
                20                  25                  30

Ala Arg Ile Leu
        35

<210> SEQ ID NO 2
<211> LENGTH: 28
<212> TYPE: PRT
<213> ORGANISM: Human immunodeficiency virus

<400> SEQUENCE: 2

Ile Glu Ala Gln Gln His Leu Leu Gln Leu Thr Val Trp Gly Ile Lys
1               5                  10                  15

Gln Leu Gln Ala Arg Ile Leu Ala Val Glu Arg Tyr
                20                  25

<210> SEQ ID NO 3
<211> LENGTH: 57
<212> TYPE: PRT
<213> ORGANISM: Human immunodeficiency virus

<400> SEQUENCE: 3

Met Gly Ala Ala Ser Met Thr Leu Thr Val Gln Ala Arg Gln Leu Leu
1               5                  10                  15

Ser Gly Ile Val Gln Gln Gln Asn Asn Leu Leu Arg Ala Ile Glu Ala
                20                  25                  30

Gln Gln His Leu Leu Gln Leu Thr Val Trp Gly Ile Lys Gln Leu Gln
                35                  40                  45

Ala Arg Ile Leu Ala Val Glu Arg Tyr
        50                  55

<210> SEQ ID NO 4
<211> LENGTH: 34
<212> TYPE: PRT
<213> ORGANISM: Human immunodeficiency virus

<400> SEQUENCE: 4

Leu Leu Glu Gln Glu Asn Lys Glu Gln Gln Asn Gln Ser Glu Glu Ile
1               5                  10                  15

Leu Ser His Ile Leu Ser Thr Tyr Asn Asn Ile Glu Arg Asp Trp Glu
                20                  25                  30

Met Trp

<210> SEQ ID NO 5
<211> LENGTH: 36
<212> TYPE: PRT
<213> ORGANISM: Human immunodeficiency virus

<400> SEQUENCE: 5

Phe Trp Asn Trp Leu Ser Ala Trp Lys Asp Leu Glu Leu Leu Glu Gln
1               5                  10                  15

Glu Asn Lys Glu Gln Gln Asn Gln Ser Glu Glu Ile Leu Ser His Ile
                20                  25                  30

Leu Ser Thr Tyr
        35

<210> SEQ ID NO 6
<211> LENGTH: 46
<212> TYPE: PRT
```

<213> ORGANISM: Human immunodeficiency virus

<400> SEQUENCE: 6

Trp Met Glu Trp Asp Arg Glu Ile Asn Asn Tyr Thr Ser Leu Ile His
1               5                   10                  15
Ser Leu Ile Glu Glu Ser Gln Asn Gln Gln Glu Lys Asn Glu Gln Glu
            20                  25                  30
Leu Leu Glu Leu Asp Lys Trp Ala Ser Leu Trp Asn Trp Phe
        35                  40                  45

<210> SEQ ID NO 7
<211> LENGTH: 38
<212> TYPE: PRT
<213> ORGANISM: Human immunodeficiency virus

<400> SEQUENCE: 7

Thr Thr Trp Met Glu Trp Asp Arg Glu Ile Asn Asn Tyr Thr Ser Leu
1               5                   10                  15
Ile His Ser Leu Ile Glu Glu Ser Gln Asn Gln Gln Glu Lys Asn Glu
            20                  25                  30
Gln Glu Leu Leu Glu Leu
        35

<210> SEQ ID NO 8
<211> LENGTH: 36
<212> TYPE: PRT
<213> ORGANISM: Human immunodeficiency virus

<400> SEQUENCE: 8

Trp Met Glu Trp Asp Arg Glu Ile Asn Asn Tyr Thr Ser Leu Ile His
1               5                   10                  15
Ser Leu Ile Glu Glu Ser Gln Asn Gln Gln Glu Lys Asn Glu Gln Glu
            20                  25                  30
Leu Leu Glu Leu
        35

<210> SEQ ID NO 9
<211> LENGTH: 28
<212> TYPE: PRT
<213> ORGANISM: Human immunodeficiency virus

<400> SEQUENCE: 9

Trp Met Glu Trp Asp Arg Glu Ile Asn Asn Tyr Thr Ser Leu Ile His
1               5                   10                  15
Ser Leu Ile Glu Glu Ser Gln Asn Gln Gln Glu Lys
            20                  25

<210> SEQ ID NO 10
<211> LENGTH: 46
<212> TYPE: PRT
<213> ORGANISM: Human immunodeficiency virus

<400> SEQUENCE: 10

Trp Met Glu Trp Asp Arg Glu Ile Asn Asn Tyr Thr Ser Leu Ile His
1               5                   10                  15
Ser Leu Ile Glu Glu Ser Gln Asn Gln Gln Glu Lys Asn Glu Gln Glu
            20                  25                  30
Leu Leu Glu Leu Asp Lys Trp Ala Ser Leu Trp Asn Trp Phe
        35                  40                  45

```
<210> SEQ ID NO 11
<211> LENGTH: 36
<212> TYPE: PRT
<213> ORGANISM: Human immunodeficiency virus

<400> SEQUENCE: 11

Ser Trp Glu Thr Trp Glu Arg Glu Ile Glu Asn Tyr Thr Lys Gln Ile
 1               5                   10                  15

Tyr Lys Ile Leu Glu Glu Ser Gln Gln Gln Asp Arg Asn Glu Lys
            20                  25                  30

Asp Leu Leu Glu
        35

<210> SEQ ID NO 12
<211> LENGTH: 38
<212> TYPE: PRT
<213> ORGANISM: Human immunodeficiency virus

<400> SEQUENCE: 12

Thr Thr Trp Glu Ala Trp Asp Arg Ala Ile Ala Glu Tyr Ala Ala Arg
 1               5                   10                  15

Ile Glu Ala Leu Leu Arg Ala Leu Gln Glu Gln Gln Glu Lys Asn Glu
            20                  25                  30

Ala Ala Leu Arg Glu Leu
        35

<210> SEQ ID NO 13
<211> LENGTH: 32
<212> TYPE: PRT
<213> ORGANISM: Human immunodeficiency virus

<400> SEQUENCE: 13

Gln Ile Trp Asn Asn Met Thr Trp Met Glu Trp Asp Arg Glu Ile Asn
 1               5                   10                  15

Asn Tyr Thr Ser Leu Ile His Ser Leu Ile Glu Glu Ser Gln Asn Gln
            20                  25                  30

<210> SEQ ID NO 14
<211> LENGTH: 30
<212> TYPE: PRT
<213> ORGANISM: Human immunodeficiency virus

<400> SEQUENCE: 14

Val Glu Asn Glu Thr Trp Met Glu Trp Glu Arg Glu Ile Glu Asn Tyr
 1               5                   10                  15

Thr Lys Leu Ile Tyr Lys Ile Leu Glu Glu Ser Gln Glu Gln
            20                  25                  30

<210> SEQ ID NO 15
<211> LENGTH: 39
<212> TYPE: PRT
<213> ORGANISM: Human immunodeficiency virus

<400> SEQUENCE: 15

Trp Gln Glu Trp Glu Gln Lys Ile Thr Ala Leu Leu Glu Gln Ala Gln
 1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35
```

```
<210> SEQ ID NO 16
<211> LENGTH: 36
<212> TYPE: PRT
<213> ORGANISM: Human immunodeficiency virus

<400> SEQUENCE: 16

Trp Met Glu Trp Asp Arg Glu Ile Glu Glu Tyr Thr Lys Lys Ile Glu
1               5                   10                  15

Glu Tyr Thr Lys Lys Ile Glu Glu Tyr Thr Lys Lys Ile Glu Glu Tyr
            20                  25                  30

Thr Lys Lys Ile
        35

<210> SEQ ID NO 17
<211> LENGTH: 16
<212> TYPE: PRT
<213> ORGANISM: Human immunodeficiency virus

<400> SEQUENCE: 17

Ser Leu Glu Gln Ile Trp Asn Asn Met Thr Trp Met Gln Trp Asp Lys
1               5                   10                  15

<210> SEQ ID NO 18
<211> LENGTH: 46
<212> TYPE: PRT
<213> ORGANISM: Human immunodeficiency virus

<400> SEQUENCE: 18

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu
        35                  40                  45

<210> SEQ ID NO 19
<211> LENGTH: 34
<212> TYPE: PRT
<213> ORGANISM: Human immunodeficiency virus

<400> SEQUENCE: 19

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg

<210> SEQ ID NO 20
<211> LENGTH: 51
<212> TYPE: PRT
<213> ORGANISM: Human immunodeficiency virus

<400> SEQUENCE: 20

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Gln Gln
    50
```

```
<210> SEQ ID NO 21
<211> LENGTH: 38
<212> TYPE: PRT
<213> ORGANISM: Human immunodeficiency virus

<400> SEQUENCE: 21

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 22
<211> LENGTH: 17
<212> TYPE: PRT
<213> ORGANISM: Human immunodeficiency virus

<400> SEQUENCE: 22

Leu Leu Gln Leu Thr Val Trp Gly Ile Lys Gln Leu Gln Ala Arg Ile
1               5                   10                  15

Leu

<210> SEQ ID NO 23
<211> LENGTH: 20
<212> TYPE: PRT
<213> ORGANISM: Human immunodeficiency virus

<400> SEQUENCE: 23

Leu Glu Ala Ile Pro Cys Ser Ile Pro Pro Cys Val Phe Phe Asn Lys
1               5                   10                  15

Pro Phe Val Phe
            20

<210> SEQ ID NO 24
<211> LENGTH: 19
<212> TYPE: PRT
<213> ORGANISM: Human immunodeficiency virus

<400> SEQUENCE: 24

Leu Glu Ala Ile Pro Cys Ser Ile Pro Pro Cys Val Phe Ala Asn Lys
1               5                   10                  15

Pro Phe Val

<210> SEQ ID NO 25
<211> LENGTH: 20
<212> TYPE: PRT
<213> ORGANISM: Human immunodeficiency virus

<400> SEQUENCE: 25

Leu Glu Ala Ile Pro Cys Ser Ile Pro Pro Cys Phe Leu Phe Asn Lys
1               5                   10                  15

Pro Phe Val Phe
            20

<210> SEQ ID NO 26
<211> LENGTH: 20
<212> TYPE: PRT
<213> ORGANISM: Human immunodeficiency virus

<400> SEQUENCE: 26
```

Leu Glu Ala Ile Pro Cys Ser Ile Pro Pro Glu Phe Leu Phe Gly Lys
1               5                   10                  15

Pro Phe Val Phe
            20

<210> SEQ ID NO 27
<211> LENGTH: 42
<212> TYPE: DNA
<213> ORGANISM: Artificial Sequence
<220> FEATURE:
<223> OTHER INFORMATION: Forward primer for amplification of 2D

<400> SEQUENCE: 27
cgcggatccc atcaccatca ccatcataag aaagtggtgc tg                          42

<210> SEQ ID NO 28
<211> LENGTH: 37
<212> TYPE: DNA
<213> ORGANISM: Artificial Sequence
<220> FEATURE:
<223> OTHER INFORMATION: Reverse primer for amplification of 2D

<400> SEQUENCE: 28
cacttcctcc tcctcctatg ctggaggcct tctggaa                                37

<210> SEQ ID NO 29
<211> LENGTH: 81
<212> TYPE: DNA
<213> ORGANISM: Artificial Sequence
<220> FEATURE:
<223> OTHER INFORMATION: Forward linker for amplification of 35-mer
      linker

<400> SEQUENCE: 29
ggaggaggag gaagtggcgg cggcggctcg ggtggtggtg gttctggagg tggcggtagc       60
ggaggtggag gtagtggagg c                                                 81

<210> SEQ ID NO 30
<211> LENGTH: 79
<212> TYPE: DNA
<213> ORGANISM: Artificial Sequence
<220> FEATURE:
<223> OTHER INFORMATION: Reverse primer for amplification of 35-mer
      linker

<400> SEQUENCE: 30
gctacctccg cctcccgaac ctccgcctcc actacctcca cctccgctac cgccacctcc       60
agaaccacca ccacccgag                                                    79

<210> SEQ ID NO 31
<211> LENGTH: 86
<212> TYPE: DNA
<213> ORGANISM: Artificial Sequence
<220> FEATURE:
<223> OTHER INFORMATION: Forward primer for amplification of NBP8

<400> SEQUENCE: 31
gaggcggagg tagcacgacc tgggaagcat gggacagagc tattgctgaa tacgcagcta       60
ggatagaagc tttactcaga gcttta                                            86

<210> SEQ ID NO 32
<211> LENGTH: 80
<212> TYPE: DNA

<213> ORGANISM: Artificial Sequence
<220> FEATURE:
<223> OTHER INFORMATION: Reverse primer for amplification of NBP8

<400> SEQUENCE: 32
cggagatctc tataattccc ttaaggctgc ttcattcttt tcttgctgtt cttgtaaagc    60
tctgagtaaa gcttctatcc    80

<210> SEQ ID NO 33
<211> LENGTH: 185
<212> TYPE: PRT
<213> ORGANISM: Homo sapiens

<400> SEQUENCE: 33

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile
            180                 185

<210> SEQ ID NO 34
<211> LENGTH: 35
<212> TYPE: PRT
<213> ORGANISM: Artificial Sequence
<220> FEATURE:
<223> OTHER INFORMATION: 35-mer linker

<400> SEQUENCE: 34

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 35
<211> LENGTH: 11
<212> TYPE: PRT
<213> ORGANISM: Artificial Sequence
<220> FEATURE:

<223> OTHER INFORMATION: N-terminal amino acid sequence

<400> SEQUENCE: 35

Gly Pro Leu Gly Ser His His His His His
1               5                   10

<210> SEQ ID NO 36
<211> LENGTH: 8
<212> TYPE: PRT
<213> ORGANISM: Artificial Sequence
<220> FEATURE:
<223> OTHER INFORMATION: C-terminal amino acid sequence

<400> SEQUENCE: 36

Glu Phe Leu Glu Val Leu Phe Gln
1               5

<210> SEQ ID NO 37
<211> LENGTH: 266
<212> TYPE: PRT
<213> ORGANISM: Artificial Sequence
<220> FEATURE:
<223> OTHER INFORMATION: Amino acid sequence of 2D-NBP1

<400> SEQUENCE: 37

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
        50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Trp Met Glu Trp
    210                 215                 220

Asp Arg Glu Ile Asn Asn Tyr Thr Ser Leu Ile His Ser Leu Ile Glu
225                 230                 235                 240

Glu Ser Gln Asn Gln Gln Glu Lys Asn Glu Gln Glu Leu Leu Glu Leu
                245                 250                 255

Asp Lys Trp Ala Ser Leu Trp Asn Trp Phe

<210> SEQ ID NO 38
<211> LENGTH: 258
<212> TYPE: PRT
<213> ORGANISM: Artificial Sequence
<220> FEATURE:
<223> OTHER INFORMATION: Amino acid sequence of 2D-NBP2

<400> SEQUENCE: 38

```
Lys Lys Val Val Leu Gly Lys Lys Gly Asp Thr Val Glu Leu Thr Cys
  1               5                  10                  15

Thr Ala Ser Gln Lys Lys Ser Ile Gln Phe His Trp Lys Asn Ser Asn
             20                  25                  30

Gln Ile Lys Ile Leu Gly Asn Gln Gly Ser Phe Leu Thr Lys Gly Pro
         35                  40                  45

Ser Lys Leu Asn Asp Arg Ala Asp Ser Arg Arg Ser Leu Trp Asp Gln
     50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                 85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Ser Thr Thr Trp Met
    210                 215                 220

Glu Trp Asp Arg Glu Ile Asn Asn Tyr Thr Ser Leu Ile His Ser Leu
225                 230                 235                 240

Ile Glu Glu Ser Gln Asn Gln Gln Glu Lys Asn Glu Gln Glu Leu Leu
                245                 250                 255

Glu Leu
```

<210> SEQ ID NO 39
<211> LENGTH: 256
<212> TYPE: PRT
<213> ORGANISM: Artificial Sequence
<220> FEATURE:
<223> OTHER INFORMATION: Amino acid sequence of 2D-NBP3

<400> SEQUENCE: 39

```
Lys Lys Val Val Leu Gly Lys Lys Gly Asp Thr Val Glu Leu Thr Cys
  1               5                  10                  15

Thr Ala Ser Gln Lys Lys Ser Ile Gln Phe His Trp Lys Asn Ser Asn
             20                  25                  30

Gln Ile Lys Ile Leu Gly Asn Gln Gly Ser Phe Leu Thr Lys Gly Pro
```

```
                35                  40                  45
Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Val Gln Leu Leu
                85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
                115                 120                 125

Gln Cys Arg Ser Pro Arg Gly Lys Asn Ile Gln Gly Gly Lys Thr Leu
 130                 135                 140

Ser Val Ser Gln Leu Glu Leu Gln Asp Ser Gly Thr Trp Thr Cys Thr
 145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
                180                 185                 190

Gly Gly Ser Gly Gly Gly Gly Ser Gly Gly Gly Gly Ser Gly Gly Gly
                195                 200                 205

Gly Ser Gly Gly Gly Gly Ser Gly Gly Gly Gly Ser Trp Met Glu Trp
 210                 215                 220

Asp Arg Glu Ile Asn Asn Tyr Thr Ser Leu Ile His Ser Leu Ile Glu
225                  230                 235                 240

Glu Ser Gln Asn Gln Gln Glu Lys Asn Glu Gln Leu Leu Glu Leu
                245                 250                 255

<210> SEQ ID NO 40
<211> LENGTH: 254
<212> TYPE: PRT
<213> ORGANISM: Artificial Sequence
<220> FEATURE:
<223> OTHER INFORMATION: Amino acid sequence of 2D-NBP4

<400> SEQUENCE: 40

Lys Lys Val Val Leu Gly Lys Lys Gly Asp Thr Val Glu Leu Thr Cys
 1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
                35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Val Gln Leu Leu
                85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
                115                 120                 125

Gln Cys Arg Ser Pro Arg Gly Lys Asn Ile Gln Gly Gly Lys Thr Leu
 130                 135                 140

Ser Val Ser Gln Leu Glu Leu Gln Asp Ser Gly Thr Trp Thr Cys Thr
```

```
145                 150                 155                 160
Val Leu Gln Asn Gln Lys Lys Val Glu Phe Lys Ile Asp Ile Val Val
                165                 170                 175
Leu Ala Phe Gln Lys Ala Ser Ser Ile Gly Gly Gly Ser Gly Gly
                180                 185                 190
Gly Gly Ser Gly Gly Gly Gly Ser Gly Gly Gly Ser Gly Gly
                195                 200                 205
Gly Ser Gly Gly Gly Ser Gly Gly Gly Ser Trp Met Glu Trp
225                 210                 215                 220
Asp Arg Glu Ile Asn Asn Tyr Thr Ser Leu Ile His Ser Leu Ile Glu
225                 230                 235                 240
Glu Ser Gln Asn Gln Gln Lys Asn Glu Gln Glu Leu Leu
                245                 250

<210> SEQ ID NO 41
<211> LENGTH: 248
<212> TYPE: PRT
<213> ORGANISM: Artificial Sequence
<220> FEATURE:
<223> OTHER INFORMATION: Amino acid sequence of 2D-NBP5

<400> SEQUENCE: 41

Lys Lys Val Val Leu Gly Lys Lys Gly Asp Thr Val Glu Leu Thr Cys
1                   5                   10                  15
Thr Ala Ser Gln Lys Lys Ser Ile Gln Phe His Trp Lys Asn Ser Asn
                20                  25                  30
Gln Ile Lys Ile Leu Gly Asn Gln Gly Ser Phe Leu Thr Lys Gly Pro
            35                  40                  45
Ser Lys Leu Asn Asp Arg Ala Asp Ser Arg Arg Ser Leu Trp Asp Gln
        50                  55                  60
Gly Asn Phe Pro Leu Ile Ile Lys Asn Leu Lys Ile Glu Asp Ser Asp
65                  70                  75                  80
Thr Tyr Ile Cys Glu Val Glu Asp Gln Lys Glu Glu Val Gln Leu Leu
                85                  90                  95
Val Phe Gly Leu Thr Ala Asn Ser Asp Thr His Leu Leu Gln Gly Gln
                100                 105                 110
Ser Leu Thr Leu Thr Leu Glu Ser Pro Pro Gly Ser Ser Pro Ser Val
                115                 120                 125
Gln Cys Arg Ser Pro Arg Gly Lys Asn Ile Gln Gly Gly Lys Thr Leu
            130                 135                 140
Ser Val Ser Gln Leu Glu Leu Gln Asp Ser Gly Thr Trp Thr Cys Thr
145                 150                 155                 160
Val Leu Gln Asn Gln Lys Lys Val Glu Phe Lys Ile Asp Ile Val Val
                165                 170                 175
Leu Ala Phe Gln Lys Ala Ser Ser Ile Gly Gly Gly Ser Gly Gly
                180                 185                 190
Gly Gly Ser Gly Gly Gly Gly Ser Gly Gly Gly Ser Gly Gly
                195                 200                 205
Gly Ser Gly Gly Gly Ser Gly Gly Gly Ser Trp Met Glu Trp
                210                 215                 220
Asp Arg Glu Ile Asn Asn Tyr Thr Ser Leu Ile His Ser Leu Ile Glu
225                 230                 235                 240
Glu Ser Gln Asn Gln Gln Glu Lys
                245
```

<210> SEQ ID NO 42
<211> LENGTH: 266
<212> TYPE: PRT
<213> ORGANISM: Artificial Sequence
<220> FEATURE:
<223> OTHER INFORMATION: Amino acid sequence of 2D-NBP6

<400> SEQUENCE: 42

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly
        195                 200                 205

Gly Ser Gly Gly Gly Ser Gly Gly Gly Ser Trp Met Glu Trp
    210                 215                 220

Asp Arg Glu Ile Asn Asn Tyr Thr Ser Leu Ile His Ser Leu Ile Glu
225                 230                 235                 240

Glu Ser Gln Asn Gln Gln Lys Asn Glu Gln Glu Leu Leu Glu Leu
                245                 250                 255

Asp Lys Trp Ala Ser Leu Trp Asn Trp Phe
            260                 265
```

<210> SEQ ID NO 43
<211> LENGTH: 256
<212> TYPE: PRT
<213> ORGANISM: Artificial Sequence
<220> FEATURE:
<223> OTHER INFORMATION: Amino acid sequence of 2D-NBP7

<400> SEQUENCE: 43

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45
```

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                     85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly
        195                 200                 205

Gly Ser Gly Gly Gly Ser Gly Gly Gly Ser Ser Trp Glu Thr
    210                 215                 220

Trp Glu Arg Glu Ile Glu Asn Tyr Thr Lys Gln Ile Tyr Lys Ile Leu
225                 230                 235                 240

Glu Glu Ser Gln Glu Gln Gln Asp Arg Asn Glu Lys Asp Leu Leu Glu
                245                 250                 255

<210> SEQ ID NO 44
<211> LENGTH: 258
<212> TYPE: PRT
<213> ORGANISM: Artificial Sequence
<220> FEATURE:
<223> OTHER INFORMATION: Amino acid sequence of 2D-NBP8

<400> SEQUENCE: 44

Lys Lys Val Val Leu Gly Lys Lys Gly Asp Thr Val Glu Leu Thr Cys
 1               5                  10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                     85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Thr Thr Trp Glu
        210                 215                 220

Ala Trp Asp Arg Ala Ile Ala Glu Tyr Ala Ala Arg Ile Glu Ala Leu
225                 230                 235                 240

Leu Arg Ala Leu Gln Glu Gln Gln Glu Lys Asn Glu Ala Ala Leu Arg
                245                 250                 255

Glu Leu

<210> SEQ ID NO 45
<211> LENGTH: 255
<212> TYPE: PRT
<213> ORGANISM: Artificial Sequence
<220> FEATURE:
<223> OTHER INFORMATION: Amino acid sequence of 2D-NBP9

<400> SEQUENCE: 45

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Trp Glu Trp
        210                 215                 220

Asp Lys Lys Ile Glu Glu Tyr Thr Lys Lys Ile Glu Glu Leu Ile Lys
225                 230                 235                 240

Lys Ser Glu Glu Gln Gln Lys Lys Asn Glu Glu Glu Leu Lys Lys
                245                 250                 255

```
<210> SEQ ID NO 46
<211> LENGTH: 252
<212> TYPE: PRT
<213> ORGANISM: Artificial Sequence
<220> FEATURE:
<223> OTHER INFORMATION: Amino acid sequence of 2D-NBP10

<400> SEQUENCE: 46

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly
        195                 200                 205

Gly Ser Gly Gly Gly Ser Gly Gly Gly Ser Gln Ile Trp Asn
    210                 215                 220

Asn Met Thr Trp Met Glu Trp Asp Arg Glu Ile Asn Asn Tyr Thr Ser
225                 230                 235                 240

Leu Ile His Ser Leu Ile Glu Glu Ser Gln Asn Gln
                245                 250

<210> SEQ ID NO 47
<211> LENGTH: 250
<212> TYPE: PRT
<213> ORGANISM: Artificial Sequence
<220> FEATURE:
<223> OTHER INFORMATION: Amino acid sequence of 2D-NBP11

<400> SEQUENCE: 47

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60
```

```
Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                 85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Val Glu Asn Glu
    210                 215                 220

Thr Trp Met Glu Trp Glu Arg Glu Ile Glu Asn Tyr Thr Lys Leu Ile
225                 230                 235                 240

Tyr Lys Ile Leu Glu Glu Ser Gln Glu Gln
                245                 250

<210> SEQ ID NO 48
<211> LENGTH: 259
<212> TYPE: PRT
<213> ORGANISM: Artificial Sequence
<220> FEATURE:
<223> OTHER INFORMATION: Amino Acid sequence of NBP12

<400> SEQUENCE: 48

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                 85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175
```

```
Leu Ala Phe Gln Lys Ala Ser Ser Ile Gly Gly Gly Ser Gly Gly
                180                 185                 190

Gly Gly Ser Gly Gly Gly Ser Gly Gly Gly Ser Gly Gly Gly
            195                 200                 205

Gly Ser Gly Gly Gly Ser Gly Gly Gly Ser Trp Gln Glu Trp
        210                 215                 220

Glu Gln Lys Ile Thr Ala Leu Leu Glu Gln Ala Gln Ile Gln Gln Glu
225                 230                 235                 240

Lys Asn Glu Tyr Glu Leu Gln Lys Leu Asp Lys Trp Ala Ser Leu Trp
                245                 250                 255

Glu Trp Phe

<210> SEQ ID NO 49
<211> LENGTH: 256
<212> TYPE: PRT
<213> ORGANISM: Artificial Sequence
<220> FEATURE:
<223> OTHER INFORMATION: Amino acid sequence of 2D-NBP13

<400> SEQUENCE: 49

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
            195                 200                 205

Gly Ser Gly Gly Gly Ser Gly Gly Gly Ser Trp Met Glu Trp
        210                 215                 220

Asp Arg Glu Ile Glu Glu Tyr Thr Lys Lys Ile Glu Glu Tyr Thr Lys
225                 230                 235                 240

Lys Ile Glu Glu Tyr Thr Lys Lys Ile Glu Glu Tyr Thr Lys Lys Ile
                245                 250                 255

<210> SEQ ID NO 50
<211> LENGTH: 236
<212> TYPE: PRT
```

-continued

```
<213> ORGANISM: Artificial Sequence
<220> FEATURE:
<223> OTHER INFORMATION: Amino acid sequence of 2D-NBP14

<400> SEQUENCE: 50

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly
        195                 200                 205

Gly Ser Gly Gly Gly Ser Gly Gly Gly Ser Ser Leu Glu Gln
    210                 215                 220

Ile Trp Asn Asn Met Thr Trp Met Gln Trp Asp Lys
225                 230                 235

<210> SEQ ID NO 51
<211> LENGTH: 256
<212> TYPE: PRT
<213> ORGANISM: Artificial Sequence
<220> FEATURE:
<223> OTHER INFORMATION: Amino acid sequence of 2D-NBP15

<400> SEQUENCE: 51

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95
```

```
Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
        130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Ser Tyr Thr Ser Leu
        210                 215                 220

Ile His Ser Leu Ile Glu Glu Ser Gln Asn Gln Gln Glu Lys Asn Glu
225                 230                 235                 240

Gln Glu Leu Leu Glu Leu Asp Lys Trp Ala Ser Leu Trp Asn Trp Phe
                245                 250                 255
```

<210> SEQ ID NO 52
<211> LENGTH: 266
<212> TYPE: PRT
<213> ORGANISM: Artificial Sequence
<220> FEATURE:
<223> OTHER INFORMATION: Amino acid sequence of 2D-CBP1

<400> SEQUENCE: 52

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
        130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Gly Ser Gly Gly
            180                 185                 190

Gly Gly Ser Gly Gly Gly Gly Ser Gly Gly Gly Gly Ser Gly Gly Gly
        195                 200                 205
```

```
Gly Ser Gly Gly Gly Gly Ser Gly Gly Gly Ser Thr Leu Thr Val
        210                 215                 220

Gln Ala Arg Gln Leu Leu Ser Gly Ile Val Gln Gln Asn Asn Leu
225                 230                 235                 240

Leu Arg Ala Ile Glu Ala Gln Gln His Leu Leu Gln Leu Thr Val Trp
                245                 250                 255

Gly Ile Lys Gln Leu Gln Ala Arg Ile Leu
                260                 265

<210> SEQ ID NO 53
<211> LENGTH: 256
<212> TYPE: PRT
<213> ORGANISM: Artificial Sequence
<220> FEATURE:
<223> OTHER INFORMATION: Amino acid sequence of 2D-CBP2

<400> SEQUENCE: 53

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Gly Ser Gly Gly Gly Ser Gly Gly Gly
        195                 200                 205

Gly Ser Gly Gly Gly Ser Gly Gly Gly Ser Ser Gly Ile Val
        210                 215                 220

Gln Gln Gln Asn Asn Leu Leu Arg Ala Ile Glu Ala Gln Gln His Leu
225                 230                 235                 240

Leu Gln Leu Thr Val Trp Gly Ile Lys Gln Leu Gln Ala Arg Ile Leu
                245                 250                 255

<210> SEQ ID NO 54
<211> LENGTH: 254
<212> TYPE: PRT
<213> ORGANISM: Artificial Sequence
<220> FEATURE:
<223> OTHER INFORMATION: Amino acid sequence of 2D-CBP3

<400> SEQUENCE: 54
```

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Gly Ser Gly Gly Gly Gly Ser Gly Gly Gly
            195                 200                 205

Gly Ser Gly Gly Gly Ser Gly Gly Gly Ser Ser Gly Ile Val
            210                 215                 220

Gln Gln Gln Asn Asn Leu Leu Arg Ala Ile Glu Ala Gln Gln His Leu
225                 230                 235                 240

Leu Gln Leu Thr Val Trp Gly Ile Lys Gln Leu Gln Ala Arg
            245                 250

<210> SEQ ID NO 55
<211> LENGTH: 271
<212> TYPE: PRT
<213> ORGANISM: Artificial Sequence
<220> FEATURE:
<223> OTHER INFORMATION: Amino acid sequence of 2D-CBP4

<400> SEQUENCE: 55

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
            195                 200                 205

Gly Ser Gly Gly Gly Ser Gly Gly Gly Ser Gln Ala Arg Gln
            210                 215                 220

Leu Leu Ser Gly Ile Val Gln Gln Asn Asn Leu Leu Arg Ala Ile
225                 230                 235                 240

Glu Ala Gln Gln His Leu Leu Gln Leu Thr Val Trp Gly Ile Lys Gln
                245                 250                 255

Leu Gln Ala Arg Ile Leu Ala Val Glu Arg Tyr Leu Lys Gln Gln
            260                 265                 270

<210> SEQ ID NO 56
<211> LENGTH: 258
<212> TYPE: PRT
<213> ORGANISM: Artificial Sequence
<220> FEATURE:
<223> OTHER INFORMATION: Amino acid sequence of 2D-CBP5

<400> SEQUENCE: 56

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
            195                 200                 205

Gly Ser Gly Gly Gly Ser Gly Gly Gly Ser Asn Asn Leu Leu
            210                 215                 220

Arg Ala Ile Glu Ala Gln His Leu Leu Gln Leu Thr Val Trp Gly
225                 230                 235                 240

Ile Lys Gln Leu Gln Ala Arg Ile Leu Ala Val Glu Arg Tyr Leu Lys
                245                 250                 255

Asp Gln

<210> SEQ ID NO 57
<211> LENGTH: 237
<212> TYPE: PRT
<213> ORGANISM: Artificial Sequence
<220> FEATURE:
<223> OTHER INFORMATION: Amino acid sequence of 2D-CBP6

<400> SEQUENCE: 57

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Leu Leu Gln Leu
    210                 215                 220

Thr Val Trp Gly Ile Lys Gln Leu Gln Ala Arg Ile Leu
225                 230                 235

<210> SEQ ID NO 58
<211> LENGTH: 248
<212> TYPE: PRT
<213> ORGANISM: Artificial Sequence
<220> FEATURE:
<223> OTHER INFORMATION: Amino acid sequence of 2D-CBP7

<400> SEQUENCE: 58

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                   70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
            180                 185                 190

Gly Gly Ser Gly Gly Gly Ser Gly Gly Gly Ser Gly Gly Gly
            195                 200                 205

Gly Ser Gly Gly Gly Ser Gly Gly Gly Ser Ile Glu Ala Gln
210                 215                 220

Gln His Leu Leu Gln Leu Thr Val Trp Gly Ile Lys Gln Leu Gln Ala
225                 230                 235                 240

Arg Ile Leu Ala Val Glu Arg Tyr
                245

<210> SEQ ID NO 59
<211> LENGTH: 240
<212> TYPE: PRT
<213> ORGANISM: Artificial Sequence
<220> FEATURE:
<223> OTHER INFORMATION: Amino acid sequence of 2D-FBP1

<400> SEQUENCE: 59

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                   70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

```
Gln Cys Arg Ser Pro Arg Gly Lys Asn Ile Gln Gly Gly Lys Thr Leu
        130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
                180                 185                 190

Gly Gly Ser Gly Gly Gly Gly Ser Gly Gly Gly Ser Gly Gly
            195                 200                 205

Gly Ser Gly Gly Gly Ser Gly Gly Gly Ser Leu Glu Ala Ile
        210                 215                 220

Pro Cys Ser Ile Pro Pro Cys Val Phe Phe Asn Lys Pro Phe Val Phe
225                 230                 235                 240

<210> SEQ ID NO 60
<211> LENGTH: 240
<212> TYPE: PRT
<213> ORGANISM: Artificial Sequence
<220> FEATURE:
<223> OTHER INFORMATION: Amino acid sequence of 2D-FBP2

<400> SEQUENCE: 60

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
        130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly
                180                 185                 190

Gly Gly Ser Gly Gly Gly Gly Ser Gly Gly Gly Ser Gly Gly Gly
            195                 200                 205

Gly Ser Gly Gly Gly Ser Gly Gly Gly Ser Leu Glu Ala Ile
        210                 215                 220

Pro Cys Ser Ile Pro Pro Cys Val Phe Ala Asn Lys Pro Phe Val Phe
225                 230                 235                 240

<210> SEQ ID NO 61
```

```
<211> LENGTH: 240
<212> TYPE: PRT
<213> ORGANISM: Artificial Sequence
<220> FEATURE:
<223> OTHER INFORMATION: Amino acid sequence of 2D-FBP3

<400> SEQUENCE: 61
```

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Gly Gly Gly Ser Gly Gly Gly
            180                 185                 190

Gly Gly Ser Gly Gly Gly Gly Ser Gly Gly Gly Ser Gly Gly Gly
        195                 200                 205

Gly Ser Gly Gly Gly Ser Gly Gly Gly Ser Leu Glu Ala Ile
    210                 215                 220

Pro Cys Ser Ile Pro Pro Cys Phe Leu Phe Asn Lys Pro Phe Val Phe
225                 230                 235                 240

```
<210> SEQ ID NO 62
<211> LENGTH: 240
<212> TYPE: PRT
<213> ORGANISM: Artificial Sequence
<220> FEATURE:
<223> OTHER INFORMATION: Amino acid sequence of 2D-FBP4

<400> SEQUENCE: 62
```

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu

```
                         85                  90                  95
Val Phe Gly Leu Thr Ala Asn Ser Asp Thr His Leu Leu Gln Gly

2. The pharmaceutical composition of claim 1 wherein said composition further includes at least one pharmaceutically acceptable excipient.

3. A method of treating a viral infection comprising:
administering an effective dose of the pharmaceutical composition of claim 1 to an individual exposed to an HIV infection;
inactivating said HIV, and
blocking entry of said HIV into a target cell, thereby treating said viral infection.

* * * * *